US011648236B2

(12) United States Patent
Steiner et al.

(10) Patent No.: US 11,648,236 B2
(45) Date of Patent: May 16, 2023

(54) METHODS OF TREATING CORONAVIRUS

(71) Applicant: VERU INC., Miami, FL (US)

(72) Inventors: Mitchell S. Steiner, Germantown, TN (US); Kester Gary Barnette, Wake Forest, NC (US)

(73) Assignee: VERU INC., Miami, FL (US)

( * ) Notice: Subject to any disclaimer, the term of this patent is extended or adjusted under 35 U.S.C. 154(b) by 68 days.

(21) Appl. No.: 17/222,835

(22) Filed: Apr. 5, 2021

(65) Prior Publication Data
US 2021/0308105 A1    Oct. 7, 2021

Related U.S. Application Data

(60) Provisional application No. 63/145,886, filed on Feb. 4, 2021, provisional application No. 63/004,781, filed on Apr. 3, 2020.

(51) Int. Cl.
| *A61K 31/4178* | (2006.01) |
| *A61K 45/06* | (2006.01) |
| *A61P 31/14* | (2006.01) |
| *A61K 31/706* | (2006.01) |
| *A61K 31/573* | (2006.01) |

(52) U.S. Cl.
CPC ........ *A61K 31/4178* (2013.01); *A61K 31/573* (2013.01); *A61K 31/706* (2013.01); *A61K 45/06* (2013.01); *A61P 31/14* (2018.01)

(58) Field of Classification Search
CPC .................................................. A61K 31/4178
USPC .......................................................... 514/397
See application file for complete search history.

(56) References Cited

U.S. PATENT DOCUMENTS

2009/0233929 A1    9/2009   Brown et al.

OTHER PUBLICATIONS

Abdallah, Hassan H., "Theoretical study for the inhibition ability of some bioactive imidazole derivatives against the Middle-East respiratory syndrome corona virus (MERS-Co)", ZANCO Journal of Pure and Applied Sciences 2019, 31(2), pp. 71-78.
Kashyap et al., "VERU-111 suppresses tumor growth and metastatic phenotypes of cervical cancer cells through the activation of p53 signaling pathway", Cancer Lett. 2020, 470: pp. 64-74.
International Search Report dated Jun. 30, 2021 in respect of PCT International Application No. PCT/US21/25807.

*Primary Examiner* — Taofiq A Solola
(74) *Attorney, Agent, or Firm* — Mark S. Cohen; Pearl Cohen Zedek Latzer Baratz LLP

(57) ABSTRACT

The present invention relates to methods of treating coronavirus infections using compounds having anti-tubulin or tubulin disruption activity.

33 Claims, 1 Drawing Sheet

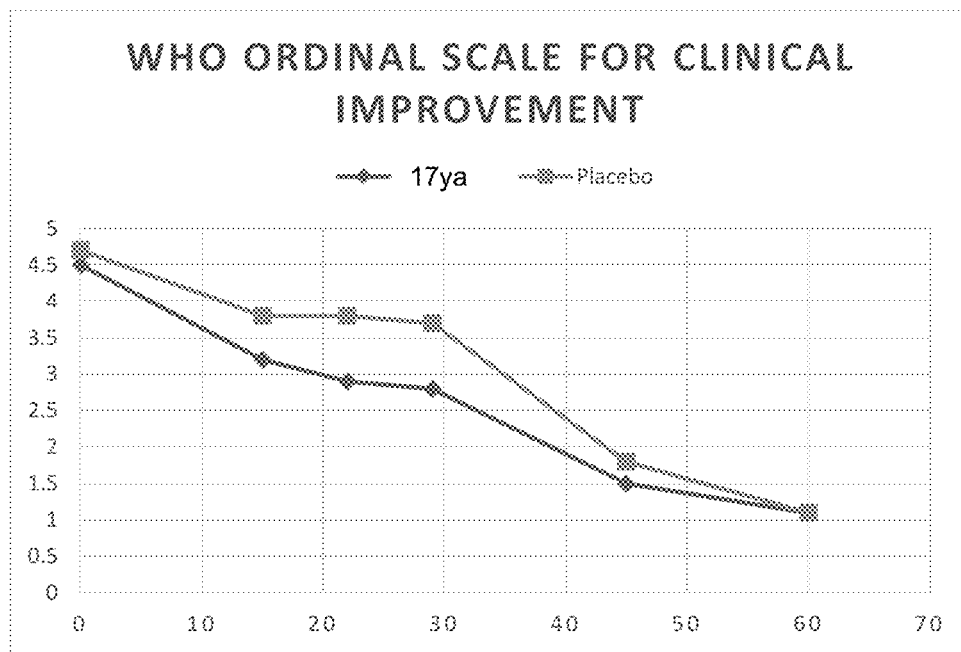

METHODS OF TREATING CORONAVIRUS

CROSS REFERENCE TO RELATED APPLICATIONS

This application claims the benefit of U.S. Provisional Application Nos. 63/004,781, filed Apr. 3, 2020; and 63/145,886, filed Feb. 4, 2021, hereby incorporated by reference.

FIELD OF THE INVENTION

The present invention is directed to methods of treating a coronavirus, using compounds having cytoskeleton disruptor activity, and formulations including the compounds with pharmaceutical acceptable excipients and/or additional cytoskeleton disruptor compounds.

BACKGROUND OF THE INVENTION

Over the last 20 years, a number of viral epidemics have posed a serious global public health risk including Severe Acute Respiratory Syndrome coronavirus (SARS-CoV) in 2002-2003, the Middle East Respiratory Syndrome coronavirus (MERS-CoV) in 2012, and Ebola in 2014-2016. On Nov. 17, 2019, a new viral acute severe respiratory disease emerged in Wuhan, China. In February 2020, World Health Organization (WHO) announced the disease's name as COVID-19 for COronaVIrus Disease first discovered in the year 2019. The coronavirus causing the disease, as it was similar to SARS-CoV, was eventually named by the International Committee on Taxonomy of Viruses (ICTV) as SARS-CoV-2. COVID-19 (SARS-CoV-2) has been declared a pandemic with over 804,061 cases and 39,074 deaths worldwide and counting as of Mar. 31, 2020. By March 2021, these numbers increased to 128,109,427 cases and 2,800,279 deaths (3%) worldwide with 103,307,591 confirmed recoveries (97%). Vaccines for SARS-CoV-2 began to be approved in the United States in December 2020 with three emergency use authorizations (EUAs) provided by March 2021; however, herd immunity has not yet reached. Despite ongoing worldwide social distancing and immunization efforts, 518,201 active cases remain including about 100,000 critically ill patients currently worldwide.

Coronaviruses are enveloped positive-sense single-stranded RNA viruses. They infect birds and mammals, especially their respiratory and gastrointestinal systems. Due to high mutation and recombination rates in coronaviruses, frequent host-shifting events from animal-to-animal and animal-to-human have occurred. Bats were identified as a natural reservoir during the severe acute respiratory syndrome (SARS) outbreak.

SARS-CoV-2, is an enveloped, nonsegmented, positive-sense, single stranded RNA virus with an unusually large RNA genome, a nucleocapsid, and club-like spikes that project from their surface called spike (S) protein. It belongs to the betacoronavirus category which includes SARS-CoV and MERS-CoV. These viruses have been responsible for epidemics with variable severity with both respiratory and extra-respiratory clinical manifestations, highly contagious, and mortality rates between 10-35%. The Coronavirus superfamily (Coronaviridae) includes several human pathogens with large RNA genomes, e.g., influenza and viral encephalitis and they are classified into alpha, beta, delta, and gamma coronavirus families and then further divided into Lineages A, B, C, and D. SARS-CoV-2 is a Lineage B betacoronavirus.

The clinical spectrum of SARS-CoV-2 varies from asymptomatic to clinical conditions characterized by pneumonia with respiratory failure necessitating mechanical ventilation and support in an intensive care unit (ICU) to sepsis, septic shock, and multiple organ failure. Chinese CDC clinical presentation reported the following disease classifications and rates of mild, severe, and critical disease in the Chinese population infected with SARS-CoV-2 in 2019-2020 which appear to be similar in other infected populations: (1) Mild disease (81%): symptoms of an upper respiratory tract viral infection, including mild fever, cough (dry), sore throat, nasal congestion, headache, muscle pain, or malaise. Signs of a more serious disease, such as dyspnea, are not present; (2) Severe disease (14%): dyspnea, respiratory frequency ≥30 breaths/min, blood oxygen saturation (SpO2)≤93%, PaO2/FiO2 ratio or P/F [the ratio between the blood pressure of the oxygen (partial pressure of oxygen, PaO2) and the percentage of oxygen supplied (fraction of inspired oxygen, FiO2)]<300, and/or lung infiltrates >50% on imaging study within 24 to 48 hours; and (3) Critical disease (5%): respiratory failure, septic shock, and/or multiple organ dysfunction. In some cases, an abnormal immune system over reaction takes place which has been labeled a 'cytokine storm. The cytokine storm is clinically manifested as an acute systemic inflammatory syndrome characterized by fever and multiple organ dysfunction. Cytokines and chemokines are induced by the viral infection which overactivates an inflammatory response (e.g., NLRP3 inflammasomes activation) which can lead to septic shock and extensive tissue damage.

The spectrum of disease and pharmacotherapy of COVID-19 as of March 2021 (unless otherwise specified) is summarized in the following paragraphs: Potential therapeutic drug classes for COVID-19 include antibody, antiviral, and anti-inflammatory therapies. Early in the time course of infection, the severity of disease is relatively minor and treatment can be focused on prevention of virus entering cells (antibody therapies) or inhibition of virus replication (antiviral therapies). In more severe cases, the patient progresses to include pulmonary infection, in which case, the addition of anti-inflammatory therapy is recommended. For example, at the time of writing, hospitalized patients typically get remdesivir (antiviral) and dexamethasone (anti-inflammatory) as standard of care, whereas mild to moderate non-hospitalized with high risk for progression to critical disease may receive an antiviral therapy alone. When pulmonary infection is present, it can progress to severe acute respiratory syndrome (SARS) in which case it is necessary to supplement oxygen including by mechanical ventilation or extracorporeal membrane oxygenation (ECMO). In this later SARS phase of COVID-19 infection, an overwhelming inflammatory response is the primary cause of damage to the respiratory system leading to acute respiratory distress syndrome (ARDS), necessitating the use of anti-inflammatory therapies which have limited efficacy data, less evidence for the efficacy of antivirals, and no promising efficacy data for antibodies in SARS.

Despite multiple EUA's and an approval, pharmacotherapeutic treatment efficacies of COVID-19 early infection and SARS are modest and drug treatment at all points in the course of disease remains an unmet clinical need. Unfortunately, the principal treatment for SARS remains supportive care and oxygen therapy for patients with severe infection. Mechanical ventilation or ECMO may be necessary in cases of respiratory failure refractory to oxygen therapy, whereas hemodynamic support is essential for managing septic shock. The overall mortality rate for individuals with a SARS-CoV-2 infection appears to be 3% to 4% and as high as 40% for patients with WHO severity scores of >4. Accordingly, current pharmacotherapeutic treatments available as of March 2021 are discussed as potential therapeutic classes. For example, only remdesivir is approved as an antiviral and has very limited efficacy, whereas dexamethasone is recommended as an EUA anti-inflammatory treatment. Further, there is a rapidly evolving series of other novel and repurposed therapies used under emergency use authorization (EUA) which is briefly summarized below. Moreover, many drugs such as hydroxychloroquine gained widespread use based on indirect evidence or case studies that were later refuted by randomized clinical trials. Others in this category include vitamins C and D, zinc, famotidine, ivermectin, ACEI/ARBs, and antibacterials such as azithromycin.

Antibody therapies such as convalescent plasma, IVIG (Intravenous IgG) (not discussed below; see PMID: 33087047 for more information), and neutralizing antibodies (casirivimab plus imdevimab; bamlanivimab; and bamlanivimab plus etesevimab) are considered most likely to be effective early in the time course of infection as these are intended to prevent cell entry by binding to and neutralizing viral spike (S) proteins, thereby blocking the binding to cell receptors and co-receptors and preventing viral entry into cells. None of the antibody therapies are FDA approved, however, several were given EUA including convalescent plasma in August 2020, both casirivimab plus imdevimab (received EUA if administered together) and bamlanivimab monotherapy in November 2020, whereas bamlanivimab plus etesevimab received EUA in February 2021. Administered early in the course of disease, FDA indicated that transfusion of high titer COVID-19 convalescent plasma had the potential for clinical benefit. Alternatively, casirivimab plus imdevimab (REGEN-COV™; two recombinant human monoclonal antibodies that bind to nonoverlapping epitopes of the spike (S) protein receptor-binding domain (RBD) of the SARS-CoV-2 virus) received EUA for the treatment of mild to moderate COVID-19 in adults, as well as in pediatric patients at least 12 years of age and weighing at least 40 kg, who have received positive results of direct SARS-CoV-2 viral testing and are at high risk for progressing to severe COVID-19 and/or hospitalization. On Mar. 23, 2021, Regeneron released Phase 3 data for a treated population of infected non-hospitalized patients (n=4,567) suggesting that this combination reduced hospitalization or death by 70% in non-hospitalized COVID-19 patients; further supporting its use in an outpatient setting (https://investor.regeneron.com/news-releases/news-release-details/phase-3-trial-shows-regen-covtm-casirivimab-imdevimab-antibody). Bamlanivimab monotherapy (a recombinant neutralising human IgG1κ monoclonal antibody that also binds to the RBD of the S protein of SARS-CoV-2 and prevents the attachment of S protein with the human ACE2 (a cell surface protein) receptor) received EUA for the same indication as REGEN-COV. EUA was also granted for the combination of bamlanivimab plus etesevimab (these bind to different but overlapping epitopes in the RBD of the S protein; using both antibodies together is expected to reduce the risk of viral resistance) for the same indication as the other synthetic neutralizing antibodies. The benefit of treatment with monoclonal neutralizing antibodies has not been observed in patients hospitalized due to COVID-19 and may be associated with worse clinical outcomes when administered to hospitalized patients requiring high flow oxygen or mechanical ventilation with COVID-19. In overview, none of the antibody therapies are FDA approved but rather some of them have EUA for use in early infection in patients at high risk for progression.

Certain hospitalized adult and pediatric COVID-19 patient populations are candidates for the only FDA approved therapy, an antiviral remdesivir (approved as Veklury). Remdesivir is a nucleotide prodrug for intravenous use that inhibits RNA polymerase of SARS-CoV-2. On Oct. 22, 2020, FDA approved Veklury (remdesivir) for use in adults and pediatric patients (12 years of age and older and weighing at least 40 kg) for the treatment of COVID-19 requiring hospitalization. Veklury should only be administered in a hospital or in a healthcare setting capable of providing acute care comparable to inpatient hospital care. This approval does not include the entire population that had been authorized to use Veklury under an EUA issued on May 1, 2020. Access for pediatric populations via the EUA continues for emergency use by licensed healthcare providers. The EUA allows treatment of suspected or laboratory-confirmed COVID-19 in hospitalized pediatric patients weighing 3.5 kg to less than 40 kg or hospitalized pediatric patients less than 12 years of age weighing at least 3.5 kg. Treatment algorithms are still uncertain for COVID-19 patients but some studies suggest modest mortality benefit of remdesivir in hypoxia patients on supplemental oxygen (ACTT-1 study) and severely ill patients not on mechanical ventilation (SIMPLE study), however, use of remdesivir in mechanically ventilated patients was not associated with a significant reduction of mortality (PMID: 33204761). Accordingly, as of January 2021, for hospitalized patients who require mechanical ventilation or ECMO, NIH recommends dexamethasone monotherapy, not Veklury mono- or combination therapy.

Critically ill patients with COVID-19 may be best served via use of dexamethasone (equivalent alternatives to dexamethasone, i.e., corticosteroids, are acceptable) since most of the damage is from immune overreaction in the lung. Though dexamethasone use via EUA continues (March 2021), the RECOVERY randomized clinical trial only demonstrated modest improvements in 28-day mortality with dexamethasone in all hospitalized patents (22.9% for dexamethasone vs. 25.7% for usual care), but improved outcomes for higher oxygenation requirement subgroups (PMID: 32678530). Similarly, treatment recommendations are stratified by oxygenation requirement with dexamethasone monotherapy is strongly recommended by NIH for those hospitalized on invasive mechanical ventilation or ECMO. Recommendations change to dexamethasone monotherapy or the addition of remdesivir for those hospitalized on non-invasive ventilation, whereas those hospitalized on supplemental oxygen can receive remdesivir or dexamethasone monotherapy, or their combination. However, dexamethasone is not recommended for those patients that are not hospitalized or hospitalized without supplemental oxygen requirement. Thus far, all recommendations are based on limited evidence and World Health Organization (WHO) recommendations differ significantly from NIH. For example, per WHO, remdesivir is not recommended regardless of severity of illness; however, WHO agrees with systemic corticosteroids for severe and critical COVID-19.

Other unapproved anti-inflammatory therapies include IL-6 inhibitors (tocilizumab), interferons, IL-1 inhibitors, and kinase inhibitors, however, as of February 2021, NIH (www.covid19treatmentguidelines.nih.gov) either indicates insufficient data or recommends against the routine use of these agents. One exception is baricitinib, a JAK inhibitor approved for rheumatoid arthritis, which as of November 2020 has EUA in combination with remdesivir for hospitalized patients with mild, moderate and severe COVID-19. EUA states for the combination is for emergency use by healthcare providers for the treatment of suspected or laboratory-confirmed COVID-19 in hospitalized adults and pediatric patients 2 years of age or older requiring supplemental oxygen, invasive mechanical ventilation, or extracorporeal membrane oxygenation (ECMO).

As can be seen, SARS-CoV-2 pharmacotherapy is based on limited data and current agents have limited efficacy at preventing early infection from progressing and decreasing mortality in SARS. Correspondingly, better SARS-CoV-2 pharmacotherapy is urgently need not just for the current global pandemic but also for future viral epidemics and pandemics, or in the case the SARS-CoV infections become endemic. The instant invention is intended to treat SARS-CoV-2 as well as future epidemics and pandemics derived from the Coronaviridae which typically produce hyperinflammatory lung infections, and despite emerging and existing therapies carry a high morbidity and mortality burden. Viruses have efficient mechanisms that take control of their host's cellular machinery to carry out viral replication, assembly, and to exit (egress) from the cell to spread infectious virions. Given the spatial distances between the point of virion entry at the plasma membrane to the location in the cell where RNA replication (nucleus) and viral assembly occur in the endoplasmic reticulum and Golgi, and then the newly generated virions have to travel back out to the plasma membrane to egress out of the cell, it is no surprise that the virus's most critical initial task is to hijack the host's internal transportation system, the cytoskeleton. The cytoskeleton is composed of three major types of protein filaments: microfilaments (actin), microtubules (tubulin), and intermediate filaments. The principal ones involved in viral replication and trafficking (transport) are microtubules and microfilaments since these are two main filament systems involved in intracellular transport.

Microtubules are important for cell shape, transport, motility, and cell division. Microtubules are dynamic long polar fibers/filaments that result from the polymerization of α and β tubulin heterodimer subunits with a positive end located at the plasma membrane and a minus end facing the nucleus at the microtubule organizing center (MTOC). From the MTOC, microtubule fibers radiate out from the nuclear area towards the periphery of the cell. Microtubules are dynamic network systems, meaning that, they undergo rapid polymerization adding α and β tubulin subunits heterodimers together to create a growing polymer chain, and subsequent rapid depolymerization (remove α and β tubulin subunits heterodimers) to deconstruct and shrink the polymer chain. This "dynamic" growing and shrinking ability of microtubules serves the constantly changing transportation requirements of the cell. Large macromolecules, like viruses, engage with specialized motor proteins (kinesins and dyneins). Kinesins and dyneins attach, carry, and move the virus cargo up and down these microtubule tracks, like train cars, to travel long distance to reach the different compartments within the cell.

As many human and animal coronaviruses originated from bats and most eukaryotic cells contain microtubules, there appears to be a conserved microtubule dependent coronavirus replication across species. Furthermore, viruses may have evolved microtubule-binding motifs or similar amino acid sequences complementary to motifs in kinesins and dyneins for successful trafficking interactions. Coronaviruses like Mouse Hepatitis Virus CoV use microtubules for neuronal spread and the Feline Infectious Peritonitis Virus (FIPV) is transported by microtubules toward the MTOC. For the porcine transmissible gastroenteritis virus (TGEV), upregulation of both α and β tubulin subunits occurs after infection. Thus, focusing on the cytoskeleton network as a drug target with the goal of impairing intracellular trafficking and disrupting virus and host interactions may be an effective way to treat coronavirus infections.

Viruses are obligate intracellular parasites, and therefore, depend solely on the cellular machinery for membrane trafficking, nuclear import and export, and gene expression. Incoming viral particles move from the cell surface to intracellular sites of viral transcription and replication. During assembly and egress, subviral nucleoprotein complexes and virions travel back to egress the plasma membrane. Because diffusion of large molecules is severely restricted in the cytoplasm, viruses use ATP-hydrolyzing molecular motors of the host for propelling along the microtubules, which are the intracellular highways.

Microtubules are cytoskeletal filaments consisting of α- and β-tubulin heterodimers and are involved in a wide range of cellular functions, including shape maintenance, vesicle transport, cell motility, and division. Tubulin is the major structural component of the microtubules and a verified target for a variety of antiviral drugs. Compounds that are able to interfere with microtubule-tubulin equilibrium in cells are effective in the treatment of viruses as a virus generally uses microtubules as a source of transportation within the cell. Other compounds that interfere with microtubule-tubulin equilibrium in cells, such as paclitaxel and vinblastine, are limited by their toxicity.

Drugs that target the cytoskeleton, especially the microtubule components, are important therapeutic agents for cancer and inflammation. The clinical activity of these compounds is dictated by the location that these compounds bind on the α and β-tubulin heterodimers that compose the microtubule filament. Three major binding sites on α and β-tubulin subunits have been identified as taxanes-, *vinca* alkaloid-, and colchicine-binding sites. Such drugs are commonly classified into two major categories: microtubule-stabilizing (e.g., taxanes) and microtubule-destabilizing, or depolymerizing agents (e.g., *vinca* alkaloids and colchicine).

Colchicine has a narrow therapeutic index with no clear distinction between nontoxic, toxic, and lethal doses. Metabolically, colchicine is eliminated via P-glycoprotein (P-gp; also known as Multi-Drug Resistance 1 (MDR1) protein). Drug-drug interactions are common with CYP3A4 and P-glycoprotein inhibitors which can increase colchicine blood concentrations to toxic levels leading to colchicine poisoning and death. Life-threatening and fatal toxicities have been observed when colchicine is administered with P-gp or strong CYP3A4 inhibitors even at approved therapeutic doses. Additional serious toxicities including myelosuppression, disseminated intravascular coagulation, and cell damage in renal, hepatic, circulatory, and central nervous systems have been observed with approved therapeutic doses of colchicine. These observed serious adverse events limit the clinical use of colchicine.

The antiviral activity of combretastatin, colchicine, and colchicine derivatives and their selected prodrugs against DENV and ZIKV in cell culture was observed at low micromolar and sub-micromolar concentrations. A major problem with taxanes, as with many biologically active natural products, is its lipophilicity and lack of solubility in aqueous systems. This leads to the use of emulsifiers like Cremophor EL and Tween 80 in clinical preparations, which leads to serious hypersensitivity reactions.

Nocodazole is a synthetic compound identified in a screen for anthelminthic agents. Nocodazole is a microtubule depolymerization agent as it binds to free tubulin heterodimers and prevents them from incorporating into microtubules. It has not been used clinically because of poor bioavailability and high toxicity.

The cellular and viral solution to master intracellular trafficking is an organized network or filaments including microtubules. Cells require microtubules for long-term normal physiology, and viruses are obligate intracellular parasites that completely depend on the physiology of the host cell. Thus, it is no surprise that most, if not all, viral life cycles require microtubules for efficient replication. The viral binding sites on microtubules might provide new targets for antiviral therapy. The inventions of this application address a novel method of interfering with microtubules of the cytoskeleton to prevent virus intracellular transportation, replication, and egress.

SUMMARY OF THE INVENTION

The invention encompasses methods of treating a coronavirus infection in a subject in need thereof by administering to the subject a formulation having a therapeutically effective amount of a compound of Formula (I)

$$\text{(A)}-X-\text{(B)}-Y-\underset{(R_1)_m}{\diagdown}\overset{R_3}{\underset{R_2}{\diagdown}} \quad \text{(I)}$$

wherein

A is phenyl, indolyl, or indazolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —OCH$_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

B is an imidazole or benzimidazole, optionally substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2$CN, hydroxyl, or $NO_2$;

$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —OCH$_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

X is a bond or NH;

Y is —C=O; and m is 1-3, or a pharmaceutically acceptable salt, hydrate, polymorph, or isomer thereof.

In an embodiment of the invention, the method encompasses compounds of Formula I wherein A is phenyl or indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —OCH$_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

B is an imidazole, optionally substituted with at least one of $(C_1-C_4)$alkyl;

$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —OCH$_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

X is a bond or NH;

Y is —C=O; and m is 1-3, or a pharmaceutically acceptable salt, hydrate, polymorph, or isomer thereof.

In another embodiment of the invention, the method encompasses compounds of Formula I wherein A is phenyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —OCH$_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

B is an imidazole, optionally substituted with at least one of $(C_1-C_4)$alkyl;

$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —OCH$_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

X is a bond or NH;

Y is —C=O; and m is 1-3, or a pharmaceutically acceptable salt, hydrate, polymorph, or isomer thereof.

In yet another embodiment of the invention, the method encompasses compounds of Formula I wherein A is indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —OCH$_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

B is an imidazole, optionally substituted with at least one of $(C_1-C_4)$alkyl;

$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —OCH$_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

X is a bond or NH;

Y is —C=O; and m is 1-3, or a pharmaceutically acceptable salt, hydrate, polymorph, or isomer thereof.

An embodiment of the invention, the method encompasses compounds of Formula I wherein A is indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —OCH$_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

B is an imidazole, optionally substituted with at least one of $(C_1-C_4)$alkyl;

$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —OCH$_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

X is a bond;
Y is —C=O; and
m is 1-3, or a pharmaceutically acceptable salt, hydrate, polymorph, or isomer thereof.

Another embodiment of the invention encompasses methods of treating a coronavirus infection in a subject in need thereof by administering to the subject a formulation having a therapeutically effective amount of a compound of the Formula VII:

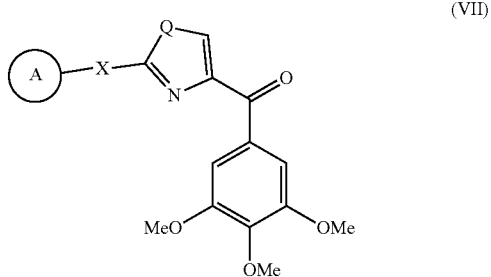

(VII)

wherein
X is a bond or NH;
Q is NH; and
A is a phenyl, indolyl, or indazolyl ring optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —CH$_2$CN, NH$_2$, hydroxyl, OC(O)CF$_3$, —OCH$_2$Ph, —NHCO—$(C_1-C_4)$alkyl, COOH, —C(O)Ph, C(O)O—$(C_1-C_4)$alkyl, C(O)H, —C(O)NH$_2$ or NO$_2$; or a pharmaceutically acceptable salt, polymorph, or isomer thereof. In another embodiment of the invention, the method encompasses compounds of Formula VII wherein X is NH. In yet another embodiment of the invention, the method encompasses compounds of Formula VII, wherein X is a bond; Q is NH; and A is an indolyl ring optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —CH$_2$CN, NH$_2$, hydroxyl, OC(O)CF$_3$, —OCH$_2$Ph, —NHCO—$(C_1-C_4)$alkyl, COOH, —C(O)Ph, C(O)O—$(C_1-C_4)$alkyl, C(O)H, —C(O)NH$_2$ or NO$_2$; or a pharmaceutically acceptable salt, hydrate, polymorph, or isomer thereof.

An embodiment of the invention encompasses methods of treating a coronavirus infection in a subject in need thereof by administering to the subject a formulation having a therapeutically effective amount of a compound of the Formula VII(c):

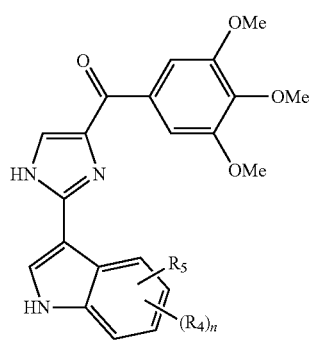

VII(c)

wherein
R$_4$ and R$_5$ independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —CH$_2$CN, NH$_2$, hydroxyl, OC(O)CF$_3$, —OCH$_2$Ph, —NHCO—$(C_1-C_4)$alkyl, COOH, —C(O)Ph, C(O)O—$(C_1-C_4)$alkyl, C(O)H, —C(O)NH$_2$ or NO$_2$; and
n is 1-4; or a pharmaceutically acceptable salt, hydrate, polymorph, or isomer thereof.

Another embodiment of the invention, encompasses methods of treating a coronavirus infection in a subject in need thereof by administering to the subject a formulation having a therapeutically effective amount of a compound 17ya represented:

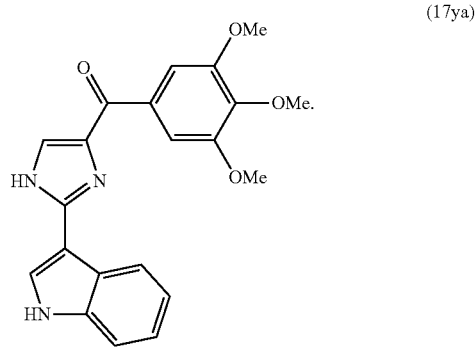 [SMILES: COc1cc(C(=O)c2c[nH]c(-c3c[nH]c4ccccc34)n2)cc(OC)c1OC]

(17ya)

Yet another embodiment of the invention encompasses methods of treating viral infections wherein the viral infection is caused by a Coronaviridae virus. An embodiment of the invention encompasses methods of treating coronavirus infections wherein the infection is caused by SARS-CoV, MERS-CoV, COVID-19 or SARS-CoV-2. Another embodiment of the invention encompasses methods of treating coronavirus infections wherein the infection is caused by COVID-19.

An embodiment of the invention encompasses methods of treating viral infections in which the infection is caused by a coronavirus. Another embodiment of the invention encompasses, methods of treating a coronavirus infection caused by SARS-CoV, MERS-CoV, or SARS-CoV-2. A preferred embodiment of the invention encompasses methods of treating a subject with SARS-CoV-2 infection. A further embodiment of the invention encompasses methods of treating a subject with SARS-CoV-2 infection at high risk for acute respiratory distress syndrome (ARDS) or severe acute respiratory syndrome (SARS). Another embodiment of the invention encompasses methods wherein treating a subject with SARS-CoV-2 infection reduces respiratory failure and/or mortality. Another embodiment of the invention encompasses methods wherein treating a subject with SARS-CoV-2 infection at high risk for acute respiratory distress syndrome (ARDS) or severe acute respiratory syndrome (SARS) reduces mortality. Another embodiment of the invention encompasses methods wherein treating a subject with SARS-CoV-2 infection reduces morbidity. Another embodiment of the invention encompasses methods wherein treating a subject with SARS-CoV-2 infection at high risk for acute respiratory distress syndrome (ARDS) or severe acute respiratory syndrome (SARS) reduces morbidity. Another embodiment of the invention encompasses methods wherein treating a subject with SARS-CoV-2 infection reduces respiratory failure, days in ICU, days on mechanical ventilator, or improves WHO Ordinal Scale for Clinical Improvements. Another embodiment of the invention encompasses methods wherein treating a subject with SARS-CoV-2 infection at high risk for acute respiratory distress syndrome (ARDS) or severe acute respiratory syndrome (SARS) reduces respiratory failure, days in ICU, days on mechanical ventilator, or improves WHO Ordinal Scale for Clinical Improvements. Another embodiment of the invention encompasses methods wherein treating a subject with SARS-CoV-2 infection reduces mortality or respiratory failure in subjects >60 years of age. Another embodiment of the invention encompasses methods wherein treating a subject with SARS-CoV-2 infection at high risk for acute respiratory distress syndrome (ARDS) or severe acute respiratory syndrome (SARS) reduces mortality or respiratory failure in subjects >60 years of age. Another embodiment of the invention encompasses methods wherein treating a subject with SARS-CoV-2 infection reduces mortality or respiratory failure when dosed in combination with remdesivir and/or dexamethasone. Another embodiment of the invention encompasses methods wherein treating a subject with SARS-CoV-2 infection at high risk for acute respiratory distress syndrome (ARDS) or severe acute respiratory syndrome (SARS) reduces mortality or respiratory failure when dosed in combination with remdesivir and/or dexamethasone. As used herein, the reduction in mortality, morbidity, or respiratory failure, days in ICU, days on mechanical ventilator, and the like means the reduction is in comparison to a subject (or subject population) treated with placebo. Likewise, any improvement, such as in WHO Ordinal Scale for Clinical Improvements, means an improvement in comparison to a subject (or subject population) treated with placebo.

Yet another embodiment of the invention, the methods further comprise at least one additional therapy. An embodiment of the method further comprises a second antiviral therapy such as a neuraminidase inhibitor, remdesivir, hydroxychloroquine, azithromycin, or hemagglutinin inhibitor. An embodiment of the method further comprises medications that modulate the immune system or host cell factors such as dexamethasone or another corticosteroid, an IL-6 inhibitor such as tocilizumab, interferons, an IL-1 inhibitor, or a kinase inhibitor such as baricitinib. Yet another embodiment of the invention, the methods further comprise an antibody therapy such as high titer COVID-19 convalescent plasma, intravenous immunoglobulin therapy (IVIG), a monoclonal antibody therapy such as casirivimab plus imdevimab, bamlanivimab, or bamlanivimab plus etesevimab. An embodiment of the method further comprises an additional therapy such as a remdesivir and/or dexamethasone or other corticosteroids. An embodiment of the method further comprises an additional therapy such as tocilizumab. An embodiment of the method further comprises an additional therapy such as baricitinib. An embodiment of the method further comprises an additional therapy such as high title COVID-19 convalescent plasma. An embodiment of the method further comprises an additional therapy such as IVIG. An embodiment of the method further comprises an additional therapy such as casirivimab plus imdevimab. An embodiment of the method further comprises an additional therapy such as bamlanivimab. An embodiment of the method further comprises an additional therapy such as bamlanivimab plus etesevimab. Yet another embodiment of the methods includes a second antiviral therapy that is at least one of favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir. Yet another embodiment of the methods includes a second therapy that is at least one of vitamins C or D, zinc, famotidine, ivermectin, or angiotensin converting enzyme inhibitor (ACEI) or angiotensin receptor binding (ARB) agent.

An embodiment of the invention encompasses methods wherein the compound of the invention is administered in an amount of about 1 mg to about 100 mg. Another embodiment of the invention encompasses methods wherein the compound of the invention is administered in an amount of about 4 to about 90 mg. Another embodiment of the invention encompasses methods wherein the compound of the invention is administered in an amount of about 9 mg to about 18 mg. Another embodiment of the invention encompasses methods wherein the compound of the invention is administered in an amount of about 4 mg to about 45 mg. In yet another embodiment of the method encompasses at least one pharmaceutically acceptable excipient.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1 illustrates the mean WHO Ordinal Scale for Clinical Improvement by Day (0=baseline). The area under the mean curve is 153 for the patient group treated with Compound 17ya and 182 for the group treated with placebo.

DETAILED DESCRIPTION OF THE INVENTION

Microtubule based macromolecule intracellular transport is a critical aspect of viral replication. For viral infection, expression of viral proteins alters the organization of these microtubular networks to serve their need to replicate and spread infectious virion. Microtubules not only facilitate infection, but microtubules are actively manipulated by viruses. Furthermore, cytoskeleton disruptor agents suppress viral infection.

Not to be limited by theory, the invention is based, in part, on the fact that tubulin interacts with the cytoplasmic domain of alphacoronavirus and betacoronavirus SARS-CoV spike S proteins. The reduction in infectious virus titer may follow by treatment with a drug that causes microtubule depolymerization, mainly because there is less S protein present at the assembly site due to impaired S protein-microtubule transport and that the incorporation process of S protein itself into virions is tubulin-dependent. Furthermore, disruption of microtubule trafficking impaired the egress out of the cell of these poorly assembled virions with less surface spike S proteins, making them less infectious. A microtubule depolymerizing agent may be effective in treating coronavirus infection by disrupting microtubule trafficking which is critical for the virus replication cycle.

The present invention is directed to antiviral therapy based upon the cytoskeleton disruptor activity of the claimed compounds that interrupts the intracellular microtubules trafficking network. Intended to overcome the disadvantages of the prior art, including but not limited to toxicity, the methods are directed to compounds specifically activated within virus-infected cell or within those cells that are preferably targeted by the virus. Not to be limited by theory, the invention is based upon virus reliance on the host cell machinery for successful replication. For instance, coronaviruses use the host secretory pathway during their replication cycle. The vesicular transport on secretory pathways is mostly mediated by microtubules and the corresponding motor proteins. The disruption of microtubules leads to decreased replication, reduced amount of released infectious particles, and decreased virus yield. Consequently, the virus load is reduced, thereby establishing an antiviral therapy. To address the need for novel, rapidly acting antiviral compounds, the inventors proposed a method of treating virus infections by the administration of the compounds described below.

In a particular embodiment, the compounds of the invention are orally bioavailable non-colchicine molecules that bind the "colchicine binding site" of α and β tubulin and inhibits tubulin polymerization at low nanomolar concentrations. These colchicine binding site inhibitors (CBSIs) have a broad scope of structures but generally possess predominantly indolyl, phenyl, or indazolyl A-rings (leftmost ring in Formula I), direct bond or amino linkers (X) between A- and B-rings, imidazole, or benzimidazole B-rings, methanone linkers (Y) between the B-ring and C-ring (rightmost ring in Formula I), and substituted phenyl C-rings. The compounds used in the methods are neither a substrate for MDRs including P-gp, MRPs, and BCRP, nor CYP3A4. The compounds used in the methods also decrease the transcription of βI, βIII, and βIV-tubulin isoforms (Li 2012). Further, the compounds used in the methods of the invention have good safety as they do not cause significant neurotoxicity, neutropenia, or myelosuppression and are well tolerated.

Further, the methods encompassed by the invention include compounds capable of influencing microtubule dynamics such that the compounds could be administered in sub-cytotoxic concentrations as systemic antiviral agents. This is in strong contrast to colchicine and other tubulin polymerization destabilizers used as antiviral drugs which possess high systemic toxicity.

The invention encompasses methods of treating a coronavirus infection in a subject in need thereof by administering to the subject a formulation having a therapeutically effective amount of a compound of Formula (I)

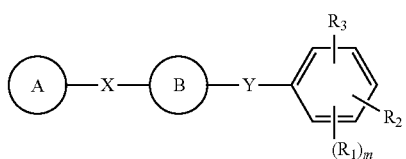

wherein
A is phenyl, indolyl, or indazolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;
B is an imidazole, thiazole, or benzimidazole, optionally substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;
X is a bond, NH, $(C_1-C_4)$alkyl, O, or S;
Y is a bond, —C═O, —C═S, $SO_2$, SO or S; and
m is 1-3, or a pharmaceutically acceptable salt, hydrate, polymorph, or isomer thereof.

The invention also encompasses methods of treating a coronavirus infection in a subject in need thereof by administering to the subject a formulation having a therapeutically effective amount of a compound of Formula (II):

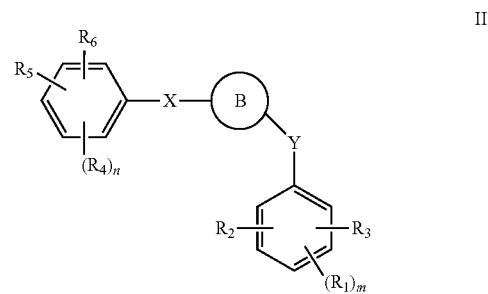

wherein
B is an imidazole, thiazole, or benzimidazole, optionally independently substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;
$R_1$, $R_2$, $R_3$, $R_4$, $R_5$ and $R_6$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;
X is a bond or NH;
Y is —C═O;
n is 1-3; and
m is 1-3; or a pharmaceutically acceptable salt, hydrate, polymorph, or isomer thereof.

The invention also encompasses methods of treating a coronavirus infection in a subject in need thereof by administering to the subject a formulation having a therapeutically effective amount of a compound of Formula (III)

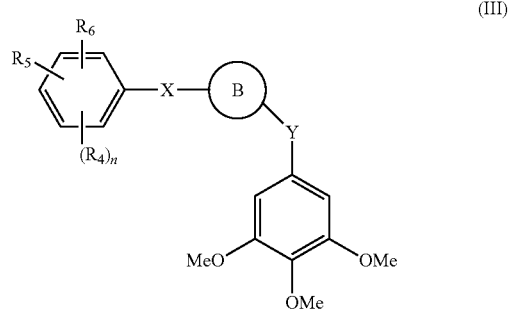

wherein

B is an imidazole, thiazole or benzimidazole, optionally independently substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_4$, $R_5$ and $R_6$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —$C(O)Ph$, $C(O)O$—$(C_1-C_4)$alkyl, $C(O)H$, —$C(O)NH_2$ or $NO_2$;

X is a bond or NH;

Y is —C=O; and n is 1-3; or a pharmaceutically acceptable salt, hydrate, polymorph, or isomer thereof.

The invention also encompasses methods of treating a coronavirus infection in a subject in need thereof by administering to the subject a formulation having a therapeutically effective amount of a compound of Formula (IV)

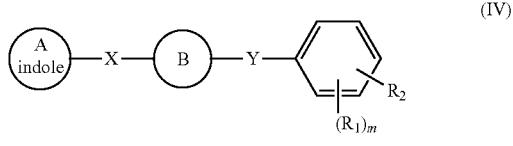

(IV)

wherein ring A is an indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —$C(O)Ph$, $C(O)O$—$(C_1-C_4)$alkyl, $C(O)H$, —$C(O)NH_2$ or $NO_2$;

B is an imidazole or benzimidazole, optionally independently substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_1$ and $R_2$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —$C(O)Ph$, $C(O)O$—$(C_1-C_4)$alkyl, $C(O)H$, —$C(O)NH_2$ or $NO_2$;

X is a bond or NH;

Y is —C=O; and m is 1-4; or a pharmaceutically acceptable salt, hydrate, polymorph, or isomer thereof.

The invention also encompasses methods of treating a coronavirus infection in a subject in need thereof by administering to the subject a formulation having a therapeutically effective amount of a compound of Formula IV(a)

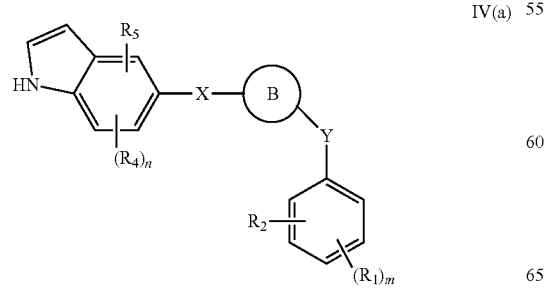

IV(a)

B is an imidazole or benzimidazole, optionally independently substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_1$, $R_2$, $R_4$ and $R_5$ are independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —$C(O)Ph$, $C(O)O$—$(C_1-C_4)$alkyl, $C(O)H$, —$C(O)NH_2$ or $NO_2$; and X is a bond or NH;

Y is —C=O; n is 1-2; and m is 1-4; or a pharmaceutically acceptable salt, hydrate, polymorph, or isomer thereof.

The invention also encompasses methods of treating a coronavirus infection in a subject in need thereof by administering to the subject a formulation having a therapeutically effective amount of a compound of Formula (V)

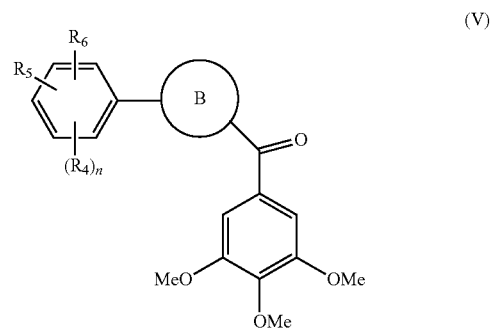

(V)

B is an imidazole or benzimidazole, optionally independently substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_4$, $R_5$ and $R_6$ are independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —$C(O)Ph$, $C(O)O$—$(C_1-C_4)$alkyl, $C(O)H$, —$C(O)NH_2$ or $NO_2$;

n is 1-3; or a pharmaceutically acceptable salt, hydrate, polymorph, or isomer thereof.

The invention also encompasses methods of treating a coronavirus infection in a subject in need thereof by administering to the subject a formulation having a therapeutically effective amount of a compound of the Formula (VI)

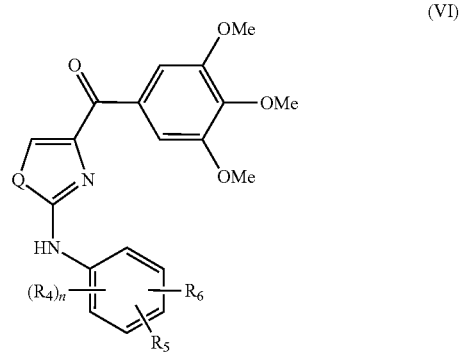

(VI)

wherein $R_4$, $R_5$ and $R_6$ are independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

Q is NH; and n is 1-3; or a pharmaceutically acceptable salt, hydrate, polymorph, or isomer thereof.

Preferably, the variables for the compounds of Formula (VIII) are $R_4$, $R_5$ and $R_6$ are independently hydrogen, $(C_1-C_4)$alkyl, halo$(C_1-C_4)$alkyl, O—$((C_1-C_4)$alkyl, $O(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$; Q is S or NH; and n is 1-3; or a pharmaceutically acceptable salt, hydrate, polymorph, or isomer thereof.

The invention also encompasses methods of treating a coronavirus infection in a subject in need thereof by administering to the subject a formulation having a therapeutically effective amount of a compound of the Formula VI in the following Table 1A:

TABLE 1A

| Formula VI | Compound | $R_4$ | $R_5$ | $R_6$ | Q |
|---|---|---|---|---|---|
| 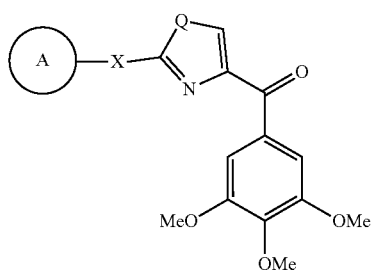 | 5e<br>n = 1 | H | H | H | N |

The invention also encompasses methods of treating a coronavirus infection in a subject in need thereof by administering to the subject a formulation having a therapeutically effective amount of a compound of the Formula VII:

(VII)

wherein

X is a bond, NH or S;

Q is NH; and

A is a phenyl, indolyl, or indazolyl ring optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$; or a pharmaceutically acceptable salt, hydrate, polymorph, or isomer thereof.

Examples of compounds of Formula VII include, but are not limited to, (2-(phenylamino)-1H-imidazol-4-yl)(3,4,5-trimethoxyphenyl)methanone (5e), (2-(phenylamino)-1H-imidazol-4-yl)(3,4,5-trimethoxyphenyl)methanone hydrochloride salt (5He), and 2-(1H-indol-3-yl)-1H-imidazol-4-yl)(3,4,5-trimethoxyphenyl)methanone (17ya).

Preferably, the variables in the compounds of Formula VII are X is a bond; Q is NH; and A is an indolyl ring optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$; or a pharmaceutically acceptable salt, hydrate, polymorph, or isomer thereof.

The invention also encompasses methods of treating a coronavirus infection in a subject in need thereof by administering to the subject a formulation having a therapeutically effective amount of a compound of the Formula VII(a):

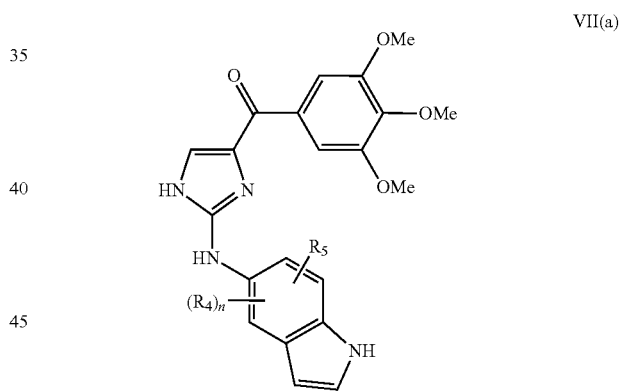

(VII(a))

wherein $R_4$ and $R_5$ are independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$; and n is 1-4; or a pharmaceutically acceptable salt, hydrate, polymorph, or isomer thereof.

The invention also encompasses methods of treating a coronavirus infection in a subject in need thereof by administering to the subject a formulation having a therapeutically effective amount of a compound of the Formula VII(b):

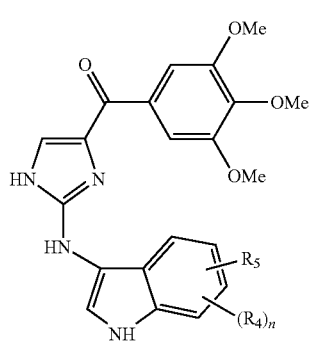

VII(b)

wherein $R_4$ and $R_5$ are independently hydrogen, $(C_1$-$C_4)$ alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$; and n is 1-4; or a pharmaceutically acceptable salt, hydrate, polymorph, or isomer thereof.

The invention also encompasses methods of treating a coronavirus infection in a subject in need thereof by administering to the subject a formulation having a therapeutically effective amount of a compound of the Formula VII(c):

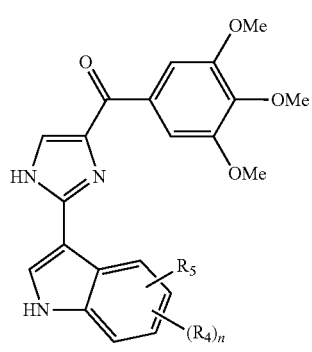

VII(c)

wherein $R_4$ and $R_5$ independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$; and n is 1-4; or a pharmaceutically acceptable salt, hydrate, polymorph, or isomer thereof. Examples of compounds of Formula XI(e) include, but are not limited to, 2-(1H-indol-3-yl)-1H-imidazol-4-yl)(3,4,5-trimethoxyphenyl)methanone (17ya).

The invention also encompasses methods of treating a coronavirus infection in a subject in need thereof by administering to the subject a formulation having a therapeutically effective amount of a compound of the Formula 17ya:

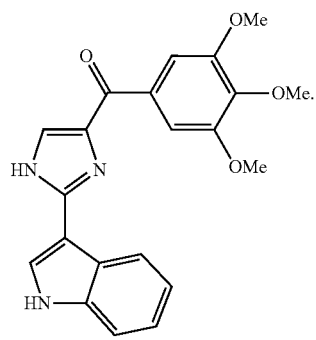

(17ya)

The invention also encompasses methods of treating a coronavirus infection in a subject in need thereof by administering to the subject a formulation having a therapeutically effective amount of a compound of the Formula in the following Table 1B:

TABLE IB

| Compound | Structure |
|---|---|
| 8 | 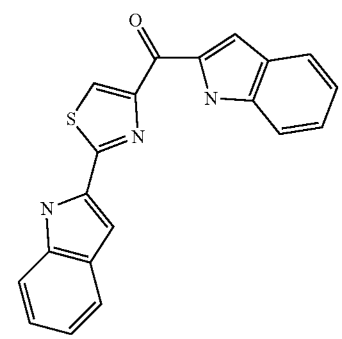 [SMILES: O=C(c1csc(-c2cc3ccccc3[nH]2)n1)c1cc2ccccc2[nH]1] |
| 9 | 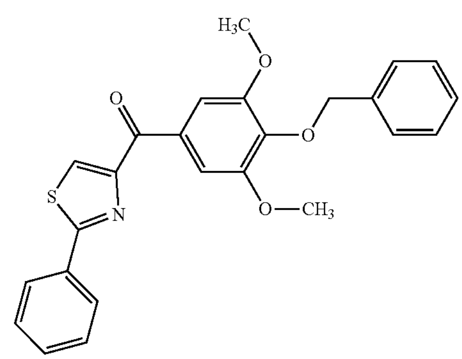 [SMILES: COc1cc(C(=O)c2csc(-c3ccccc3)n2)cc(OC)c1OCc1ccccc1] |
| 10 | 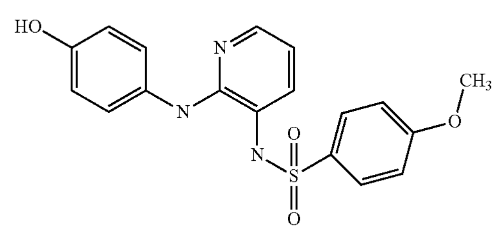 [SMILES: COc1ccc(S(=O)(=O)Nc2cccnc2Nc2ccc(O)cc2)cc1] |

TABLE IB-continued
| Compound | Structure |
|---|---|
| 11 | 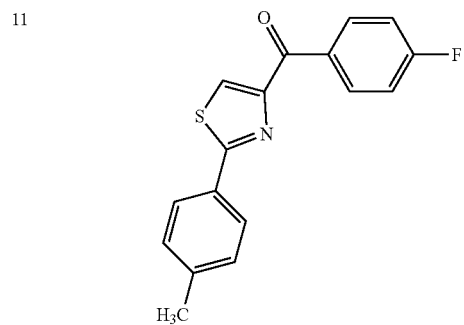 |
| 12 | 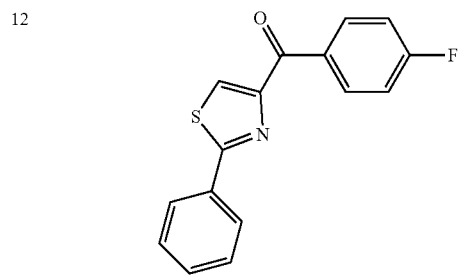 |
| 13 | 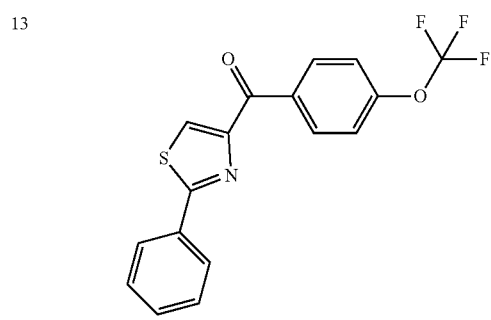 |
| 14 | 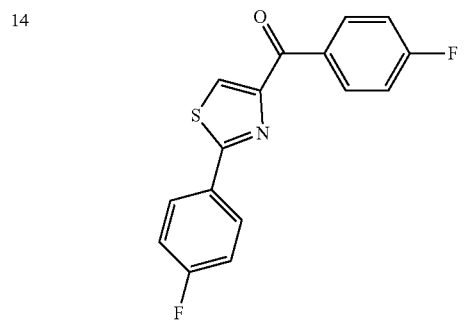 |
| 16 | 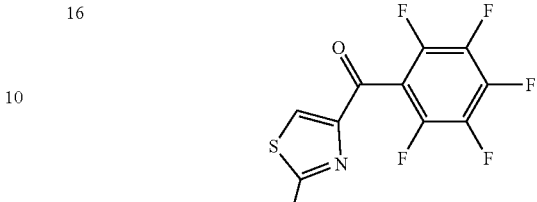 |
| 17 | 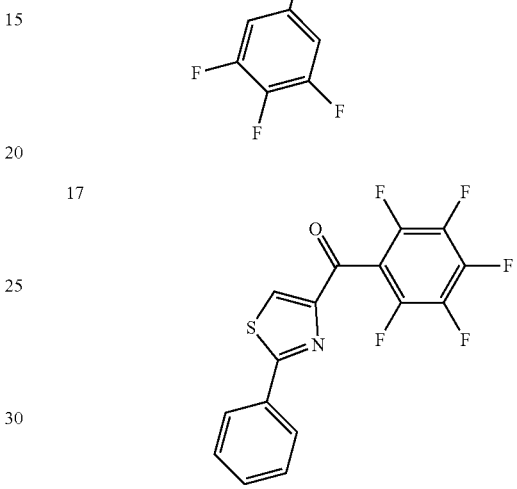 |
| 18 | 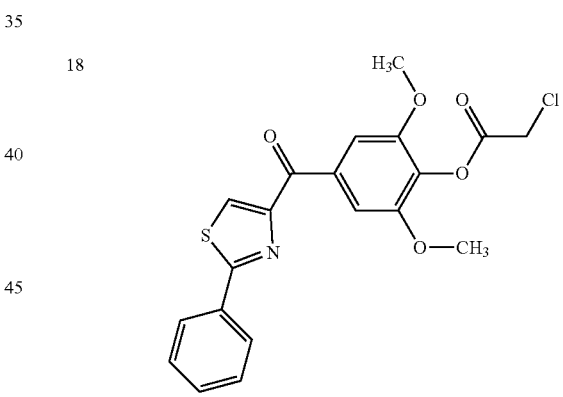 |
| 19 | 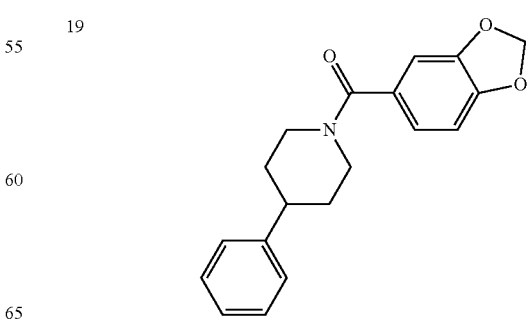 |

TABLE IB-continued
| Compound | Structure |
|---|---|
| 20 | 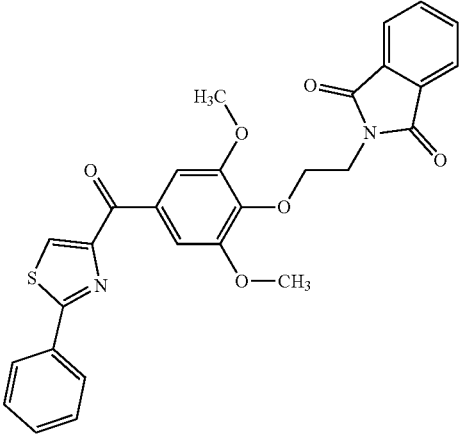 [SMILES: COc1cc(C(=O)c2csc(-c3ccccc3)n2)cc(OC)c1OCCN1C(=O)c2ccccc2C1=O] |
| 21 | 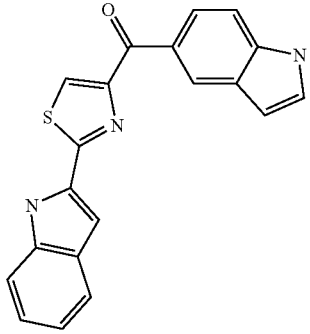 [SMILES: O=C(c1ccc2[nH]ccc2c1)c1csc(-c2cc3ccccc3[nH]2)n1] |
| 22 | 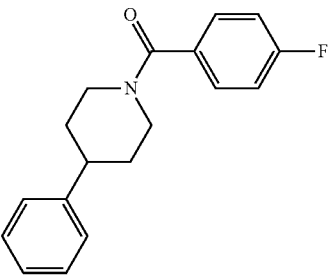 [SMILES: O=C(c1ccc(F)cc1)N1CCC(c2ccccc2)CC1] |
| 23 | 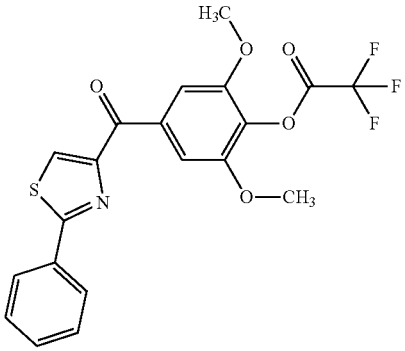 [SMILES: COc1cc(C(=O)c2csc(-c3ccccc3)n2)cc(OC)c1OC(=O)C(F)(F)F] |
| 24 | 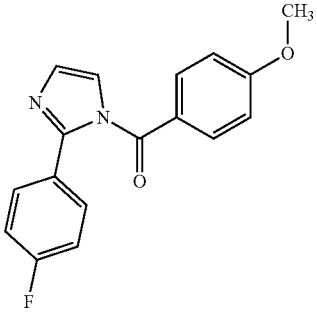 [SMILES: COc1ccc(C(=O)n2ccnc2-c2ccc(F)cc2)cc1] |
| 25 | 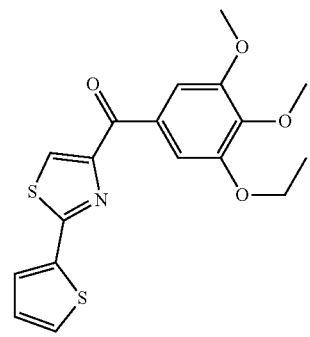 [SMILES: CCOc1cc(C(=O)c2csc(-c3cccs3)n2)cc(OC)c1OC] |
| 26 | 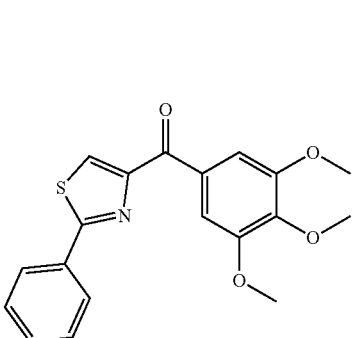 |
| 27 | 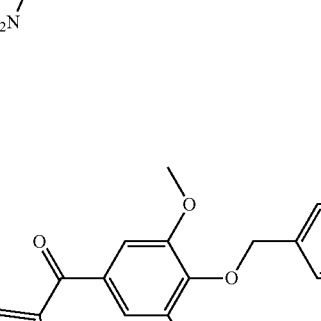 |

TABLE IB-continued

| Compound | Structure |
|---|---|
| 28 | |
| 29 | |
| 30 | |
| 32 | |
| 33 | 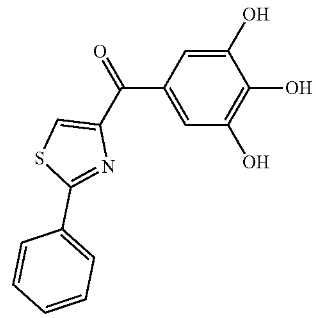 [SMILES: O=C(c1cc(O)c(O)c(O)c1)c1csc(-c2ccccc2)n1] |
| 34 | 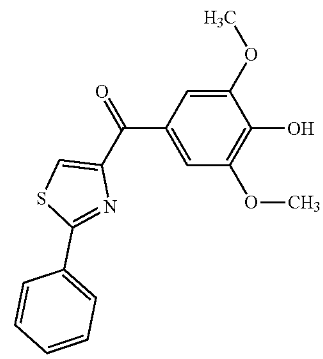 [SMILES: COc1cc(C(=O)c2csc(-c3ccccc3)n2)cc(OC)c1O] |
| 35 | 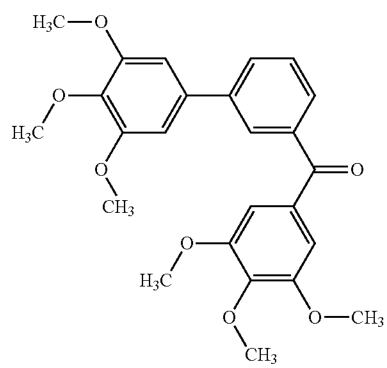 |
| 40 | 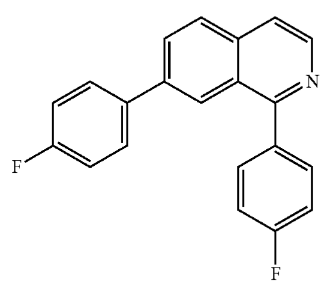 [SMILES: Fc1ccc(-c2ccc3ccnc(-c4ccc(F)cc4)c3c2)cc1] |
| 41 | 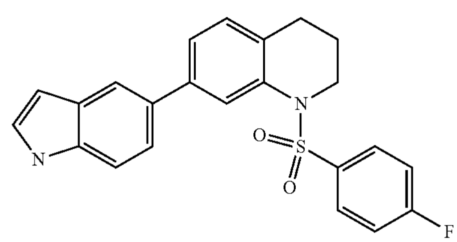 [SMILES: O=S(=O)(c1ccc(F)cc1)N1CCCc2ccc(-c3ccc4[nH]ccc4c3)cc21] |

TABLE IB-continued
| Compound | Structure |
|---|---|
| 42 | 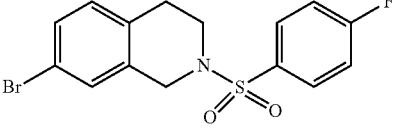 |
| 43 | 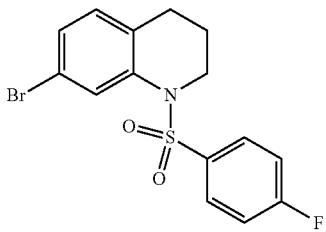 [SMILES: O=S(=O)(c1ccc(F)cc1)N1CCCc2ccc(Br)cc21] |
| 44 | 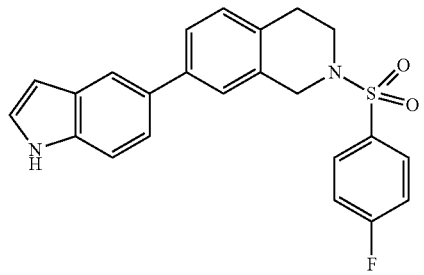 [SMILES: O=S(=O)(c1ccc(F)cc1)N1CCc2ccc(-c3ccc4[nH]ccc4c3)cc2C1] |
| 45 | 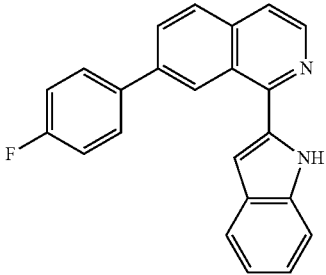 [SMILES: Fc1ccc(-c2ccc3ccnc(-c4cc5ccccc5[nH]4)c3c2)cc1] |
| 46 | 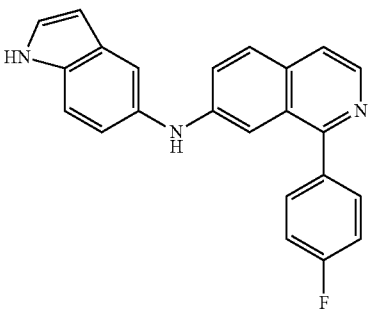 [SMILES: Fc1ccc(-c2nccc3ccc(Nc4ccc5[nH]ccc5c4)cc23)cc1] |
| 47 | 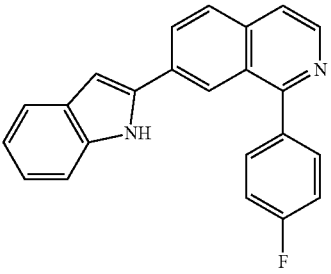 [SMILES: Fc1ccc(-c2nccc3ccc(-c4cc5ccccc5[nH]4)cc23)cc1] |
| 48 | 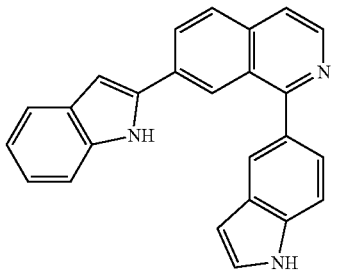 [SMILES: c1ccc2[nH]c(-c3ccc4ccnc(-c5ccc6[nH]ccc6c5)c4c3)cc2c1] |
| 49 | 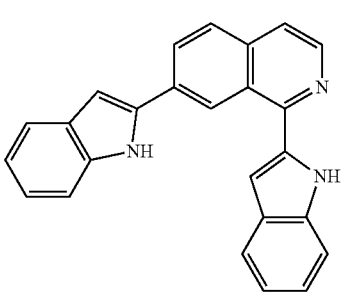 [SMILES: c1ccc2[nH]c(-c3ccc4ccnc(-c5cc6ccccc6[nH]5)c4c3)cc2c1] |
| 50 | 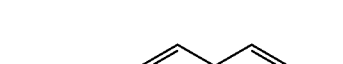 |
| 51 | 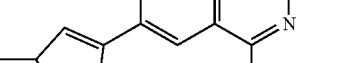 |
| 52 |  |

TABLE IB-continued

| Compound | Structure |
|---|---|
| 53 | 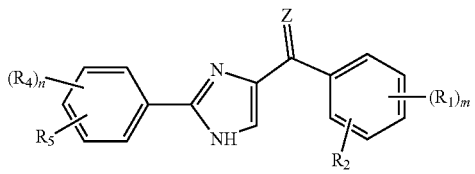 |
| 54 | 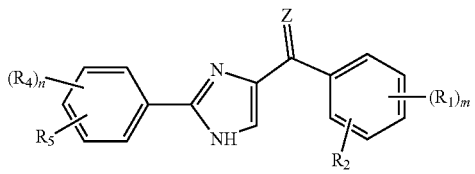 |

The invention also encompasses methods of treating a coronavirus infection in a subject in need thereof by administering to the subject a formulation having a therapeutically effective amount of a compound of the Formula XIII

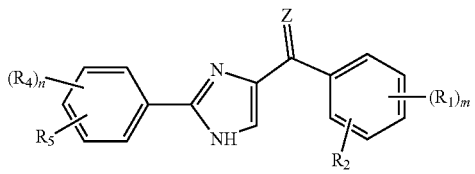

(XIII)

wherein

Z is O;

$R_1$ and $R_4$ are independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —C(O)$NH_2$ or $NO_2$;

$R_2$ and $R_5$ are independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —C(O)$NH_2$ or $NO_2$;

m is an integer between 1-4; and n is an integer between 1-4;

or a pharmaceutically acceptable salt, hydrate, polymorph, or isomer.

The invention also encompasses methods of treating a coronavirus infection in a subject in need thereof by administering to the subject a formulation having a therapeutically effective amount of a compound of the Formula XIV:

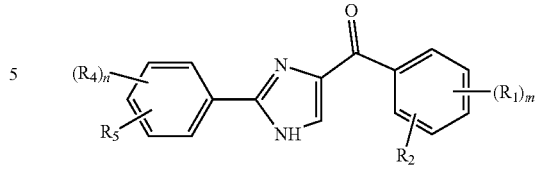

(XIV)

wherein $R_1$ and $R_4$ are independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —C(O)$NH_2$ or $NO_2$;

$R_2$ and $R_5$ are independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO— alkyl, COOH, —C(O)Ph, C(O)O—$(C_1-C_4)$alkyl, C(O)H, —C(O)$NH_2$ or $NO_2$;

m is an integer between 1-4; and n is an integer between 1-4;

or a pharmaceutically acceptable salt, hydrate, polymorph, or isomer thereof.

Non limiting examples of compounds of formula XIV are selected from: (2-phenyl-1H-imidazol-4-yl)(3,4,5-trimethoxyphenyl)methanone (12aa), (4-fluorophenyl)(2-phenyl-1H-imidazol-4-yl)methanone (12af), (2-(4-fluorophenyl)-1H-imidazol-4-yl)(3,4,5-trimethoxyphenyl) methanone (12ba), (2-(4-methoxyphenyl)-1H-imidazol-4-yl)(3,4,5-trimethoxyphenyl)methanone (12ca), (4-fluorophenyl)(2-(4-methoxyphenyl)-1H-imidazol-4-yl) methanone (12cb), (2-(p-tolyl)-1H-imidazol-4-yl)(3,4,5-trimethoxyphenyl)methanone (12da), (4-fluorophenyl)(2-(p-tolyl)-1H-imidazol-4-yl)methanone (12db), (4-hydroxy-3,5-dimethoxyphenyl)(2-(p-tolyl)-1H-imidazol-4-yl) methanone (12dc), (2-(4-chlorophenyl)-1H-imidazol-4-yl) (3,4,5-trimethoxyphenyl)methanone (12fa), (2-(4-chlorophenyl)-1H-imidazol-4-yl)(4-fluorophenyl) methanone (12fb), (2-(4-chlorophenyl)-1H-imidazol-4-yl) (4-hydroxy-3,5-dimethoxyphenyl)methanone (12fc), (2-(4-(dimethylamino)phenyl)-1H-imidazol-4-yl)(3,4,5-trimethoxyphenyl)methanone (12ga); (2-(4-(dimethylamino)phenyl)-1H-imidazol-4-yl)(4-fluorophenyl)methanone (12gb), (2-(3,4-dimethoxyphenyl)-1H-imidazol-4-yl)(3,4,5-trimethoxyphenyl)methanone (12ha), (2-(4-(benzyloxy)phenyl)-1H-imidazol-4-yl)(4-fluorophenyl)methanone (12jb), (2-(4-bromophenyl)-1H-imidazol-4-yl)(3,4,5-trimethoxyphenyl)methanone (12la), (2-(4-(trifluoromethyl)phenyl)-1H-imidazol-4-yl)(3,4,5-trimethoxyphenyl)methanone (12pa).

The invention also encompasses methods of treating a coronavirus infection in a subject in need thereof by administering to the subject a formulation having a therapeutically effective amount of a compound of the Formula XIVa:

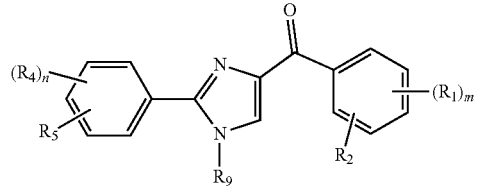

(XIVa)

wherein $R_1$ and $R_4$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$;

$R_2$ and $R_5$ are independently hydrogen, ($C_1$-$C_4$)alkyl, halo ($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$;

$R_9$ is H, linear or branched, alkyl, aryl, $CH_2Ph$, benzyl, haloalkyl, aminoalkyl, $OCH_2Ph$, $SO_2$-Aryl, —(C=O)-Aryl or OH, optionally substituted with at least one of hydrogen, hydroxyl, an aliphatic straight- or branched-chain $C_1$ to $C_{10}$ hydrocarbon, alkoxy, haloalkoxy, aryloxy, nitro, cyano, alkyl-CN, halo (e.g., F, Cl, Br, I), haloalkyl, dihaloalkyl, trihaloalkyl, COOH, C(O)Ph, C(O)-alkyl, C(O)O-alkyl, C(O)H, $C(O)NH_2$, —$OC(O)CF_3$, $OCH_2Ph$, amino, aminoalkyl, alkylamino, mesylamino, dialkylamino, arylamino, amido, NHC(O)-alkyl, urea, alkyl-urea, alkylamido (e.g., acetamide), haloalkylamido, arylamido, aryl, and $C_5$ to $C_7$ cycloalkyl, arylalkyl, and combinations thereof;

m is an integer between 1-4; and n is an integer between 1-4;

or a pharmaceutically acceptable salt, hydrate, polymorph, or isomer thereof.

Non limiting examples of compounds of formula XIVa are selected from: (4-fluorophenyl)(2-phenyl-1-(phenylsulfonyl)-1H-imidazol-4-yl)methanone (11af), (4-fluorophenyl)(2-(4-methoxyphenyl)-1-(phenylsulfonyl)-1H-imidazol-4-yl)methanone (11cb), (4-fluorophenyl)(1-(phenylsulfonyl)-2-(p-tolyl)-1H-imidazol-4-yl)methanone (11db), (2-(4-chlorophenyl)-1-(phenylsulfonyl)-1H-imidazol-4-yl)(4-fluorophenyl)methanone (11fb), (2-(4-(dimethylamino)phenyl)-1-(phenylsulfonyl)-1H-imidazol-4-yl)(3,4,5-trimethoxyphenyl)methanone (11ga), (2-(4-(dimethylamino)phenyl)-1-(phenylsulfonyl)-1H-imidazol-4-yl)(4-fluorophenyl)methanone (11gb), (2-(3,4-dimethoxyphenyl)-1-(phenylsulfonyl)-1H-imidazol-4-yl)(3,4,5-trimethoxyphenyl)methanone (11ha), (2-(4-(benzyloxy)phenyl)-1-(phenylsulfonyl)-1H-imidazol-4-yl)(4-fluorophenyl)methanone (11jb), (2-(4-(dimethylamino)phenyl)-1-((4-methoxyphenyl)sulfonyl)-1H-imidazol-4-yl)(4-fluorophenyl)methanone (12gba), (1-benzyl-2-(p-tolyl)-1H-imidazol-4-yl)(3,4,5-trimethoxyphenyl)methanone (12daa), (1-methyl-2-(p-tolyl)-1H-imidazol-4-yl)(3,4,5-trimethoxyphenyl)methanone (12dab), (4-fluorophenyl)(2-(4-methoxyphenyl)-1-methyl-1H-imidazol-4-yl)methanone (12cba).

The invention also encompasses methods of treating a coronavirus infection in a subject in need thereof by administering to the subject a formulation having a therapeutically effective amount of a compound of the Formula XV:

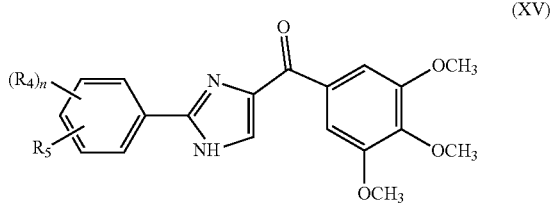

(XV)

wherein $R_4$ and $R_5$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$; and n is 1-4; or a pharmaceutically acceptable salt, hydrate, polymorph, or isomer thereof.

Non limiting examples of compounds of formula XV are selected from: (2-phenyl-1H-imidazol-4-yl)(3,4,5-trimethoxyphenyl)methanone (12aa), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (2-(p-tolyl)-1H-imidazol-4-yl)(3,4,5-trimethoxyphenyl)methanone (12da), (3,4,5-trimethoxyphenyl)(2-(3,4,5-trimethoxyphenyl)-1H-imidazol-4-yl)methanone (12ea), (2-(4-chlorophenyl)-1H-imidazol-4-yl)(3,4,5-trimethoxyphenyl)methanone (12fa), (2-(4-(dimethylamino)phenyl)-1H-imidazol-4-yl)(3,4,5-trimethoxyphenyl)methanone (12ga), (2-(3,4-dimethoxyphenyl)-1H-imidazol-4-yl)(3,4,5-trimethoxyphenyl)methanone (12ha), (2-(2-(trifluoromethyl)phenyl)-1H-imidazol-4-yl)(3,4,5-trimethoxyphenyl)methanone (12ia), (2-(4-(benzyloxy)phenyl)-1H-imidazol-4-yl)(3,4,5-trimethoxyphenyl)methanone (12ja), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (12la), and (2-(4-(trifluoromethyl)phenyl)-1H-imidazol-4-yl)(3,4,5-trimethoxyphenyl)methanone (12pa).

The invention also encompasses methods of treating a coronavirus infection in a subject in need thereof by administering to the subject a formulation having a therapeutically effective amount of a compound of the Formula XVI:

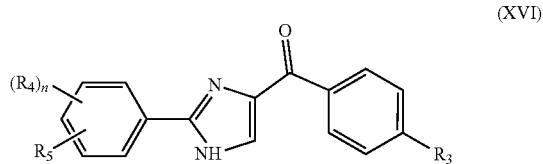

(XVI)

wherein $R_4$ and $R_5$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$;

$R_3$ is I, Br, Cl, or F; and n is 1-4; or a pharmaceutically acceptable salt, hydrate, polymorph, or isomer.

Non limiting examples of compounds of formula XVI are selected from: (4-fluorophenyl)(2-phenyl-1H-imidazol-4-yl)methanone (12af), (4-fluorophenyl)(2-(4-methoxyphenyl)-1H-imidazol-4-yl)methanone (12cb), (4-fluorophenyl)(2-(p-tolyl)-1H-imidazol-4-yl)methanone (12db), 4-fluorophenyl)(2-(3,4,5-trimethoxyphenyl)-1H-imidazol-4-yl)methanone (12eb), (2-(4-chlorophenyl)-1H-imidazol-4-yl)(4-fluorophenyl)methanone (12fb), (2-(4-(dimethylamino)phenyl)-1H-imidazol-4-yl)(4-fluorophenyl)methanone (12gb), (2-(4-(benzyloxy)phenyl)-1H-imidazol-4-yl)(4-fluorophenyl)methanone (12jb).

The invention also encompasses methods of treating a coronavirus infection in a subject in need thereof by administering to the subject a formulation having a therapeutically effective amount of a compound of the Formula XVII:

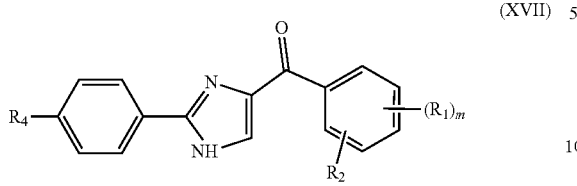

(XVII)

wherein R$_4$ is H, O—(C$_1$-C$_4$)alkyl, I, Br, Cl, F, (C$_1$-C$_4$)alkyl, halo(C$_1$-C$_4$)alkyl, amino(C$_1$-C$_4$)alkyl, OCH$_2$Ph, OH, CN, NO$_2$, —NHCO—(C$_1$-C$_4$)alkyl, COOH, C(O)O—(C$_1$-C$_4$) alkyl or C(O)H;
wherein R$_1$ and R$_2$ are independently H, O-alkyl, I, Br, Cl, F, (C$_1$-C$_4$)alkyl, halo(C$_1$-C$_4$)alkyl, amino(C$_1$-C$_4$)alkyl, OCH$_2$Ph, OH, CN, NO$_2$, —NHCO—(C$_1$-C$_4$)alkyl, COOH, C(O)O—(C$_1$-C$_4$)alkyl or C(O)H; and
m is 1-4; or a pharmaceutically acceptable salt, hydrate, polymorph, or isomer thereof.

Non limiting examples of compounds of formula XVII are selected from: (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (4-fluorophenyl)(2-(4-methoxyphenyl)-1H-imidazol-4-yl)methanone (12cb), (2-(p-tolyl)-1H-imidazol-4-yl)(3,4,5-trimethoxyphenyl)methanone (12da), (4-fluorophenyl)(2-(p-tolyl)-1H-imidazol-4-yl)methanone (12db), (4-Hydroxy-3,5-dimethoxyphenyl)(2-(p-tolyl)-1H-imidazol-4-yl)methanone (12dc), (2-(4-chlorophenyl)-1H-imidazol-4-yl)(3,4,5-trimethoxyphenyl)methanone (12fa), (2-(4-chlorophenyl)-1H-imidazol-4-yl)(4-fluorophenyl) methanone (12fb), (2-(4-chlorophenyl)-1H-imidazol-4-yl)(3,4,5-trihydroxyphenyl)methanone (13fa), (2-(4-(dimethylamino)phenyl)-1H-imidazol-4-yl)(3,4,5-trimethoxyphenyl)methanone (12ga), (2-(4-(dimethylamino)phenyl)-1H-imidazol-4-yl)(4-fluorophenyl)methanone (12gb), (2-(4-(benzyloxy)phenyl)-1H-imidazol-4-yl)(4-fluorophenyl)methanone (12jb), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (121a), (2-(4-(trifluoromethyl)phenyl)-1H-imidazol yl)(3,4,5-trimethoxyphenyl)methanone (12pa).

The invention also encompasses methods of treating a coronavirus infection in a subject in need thereof by administering to the subject a formulation having a therapeutically effective amount of a compound of the Formula XVII represented by the structure of formula 12fb:

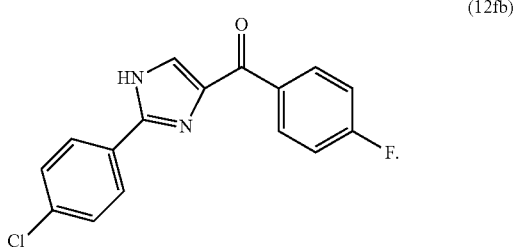 [SMILES: O=C(c1ccc(F)cc1)c1c[nH]c(-c2ccc(Cl)cc2)n1]

(12fb)

The invention also encompasses methods of treating a coronavirus infection in a subject in need thereof by administering to the subject a formulation having a therapeutically effective amount of a compound of the Formula XVII represented by the structure of formula 12cb:

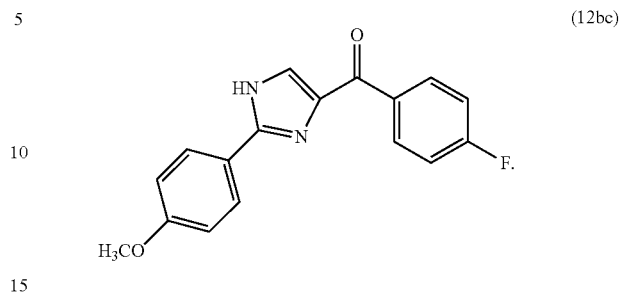

(12bc)

Non limiting examples of compounds are selected from: (4-methoxyphenyl)(2-phenyl-1H-imidazol-1-yl)methanone (12aba), (2-phenyl-1H-imidazol-1-yl)(3,4,5-trimethoxyphenyl)methanone (12aaa), 2-phenyl-1-(phenylsulfonyl)-1H-imidazole (10a), 2-(4-nitrophenyl)-1-(phenylsulfonyl)-1H-imidazole (10x), 2-(4-(benzyloxy)phenyl)-1-(phenylsulfonyl)-1H-imidazole (10j).

The invention also encompasses methods of treating a coronavirus infection in a subject in need thereof by administering to the subject a formulation having a therapeutically effective amount of a compound of the Formula XIX:

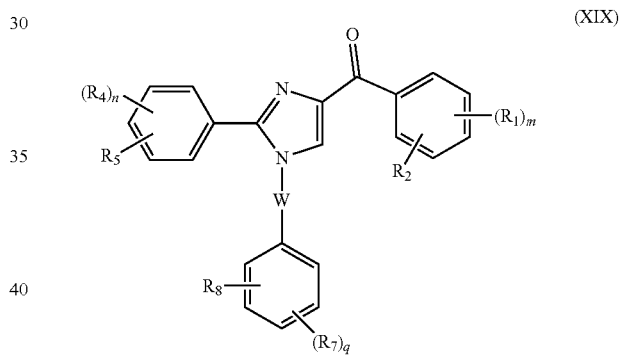

(XIX)

wherein
W is C═O, C═S, SO$_2$, S═O;
R$_1$, R$_4$ and R$_7$ are independently hydrogen, (C$_1$-C$_4$)alkyl, halo(C$_1$-C$_4$)alkyl, O—(C$_1$-C$_4$)alkyl, O—(C$_1$-C$_4$)haloalkyl, (C$_1$-C$_4$)alkylamino, amino(C$_1$-C$_4$)alkyl, F, Cl, Br, I, CN, —CH$_2$CN, NH$_2$, hydroxyl, OC(O)CF$_3$, —OCH$_2$Ph, —NHCO—(C$_1$-C$_4$)alkyl, COOH, —C(O)Ph, C(O)O—(C$_1$-C$_4$)alkyl, C(O)H, —C(O)NH$_2$ or NO$_2$;
R$_2$, R$_5$ and R$_8$ are independently hydrogen, (C$_1$-C$_4$)alkyl, halo(C$_1$-C$_4$)alkyl, O—(C$_1$-C$_4$)alkyl, O—(C$_1$-C$_4$)haloalkyl, (C$_1$-C$_4$)alkylamino, amino(C$_1$-C$_4$)alkyl, F, Cl, Br, I, CN, —CH$_2$CN, NH$_2$, hydroxyl, OC(O)CF$_3$, —OCH$_2$Ph, —NHCO—(C$_1$-C$_4$)alkyl, COOH, —C(O)Ph, C(O)O—(C$_1$-C$_4$)alkyl, C(O)H, —C(O)NH$_2$ or NO$_2$;
m is 1-4;
n is 1-4; and
q is 1-4;
or its pharmaceutically acceptable salt, hydrate, polymorph, or isomer.

Non limiting examples of compounds of formula XIX are selected from: (2-(4-(dimethylamino)phenyl)-1-((4-methoxyphenyl)sulfonyl)-1H-imidazol-4-yl)(3,4,5-trimethoxyphenyl)methanone (11gaa); (2-(4-bromophenyl)-

1-(phenylsulfonyl)-1H-imidazol-4-yl)(3,4,5-trimethoxyphenyl)methanone (11aa), (4-fluorophenyl)(2-(4-methoxyphenyl)-1-(phenylsulfonyl)-1H-imidazol-4-yl)methanone (11cb), (2-(4-chlorophenyl)-1-(phenylsulfonyl)-1H-imidazol-4-yl)(4-fluorophenyl)methanone (11fb), (4-fluorophenyl)(2-phenyl-1-(phenylsulfonyl)-1H-imidazol-4-yl)methanone (11af), (4-fluorophenyl)(1-(phenylsulfonyl)-2-(p-tolyl)-1H-imidazol-4-yl)methanone (11db), (2-(4-(dimethylamino)phenyl)-1-(phenylsulfonyl)-1H-imidazol-4-yl)(3,4,5-trimethoxyphenyl)methanone (11ga), (2-(4-(dimethylamino)phenyl)-1-(phenylsulfonyl)-1H-imidazol-4-yl)(4-fluorophenyl)methanone (11gb), (2-(3,4-dimethoxyphenyl)-1-(phenylsulfonyl)-1H-imidazol-4-yl)(3,4,5-trimethoxyphenyl)methanone (11ha), (2-(4-(benzyloxy)phenyl)-1-(phenylsulfonyl)-1H-imidazol-4-yl)(4-fluorophenyl)methanone (11jb), (2-(4-(dimethylamino)phenyl)-1-((4-methoxyphenyl) sulfonyl)-1H-imidazol yl)(4-fluorophenyl)methanone (12gba).

The invention also encompasses methods of treating a coronavirus infection in a subject in need thereof by administering to the subject a formulation having a therapeutically effective amount of a compound of the Formula XIX represented by the structure of formula 11cb:

(11cb)

The invention also encompasses methods of treating a coronavirus infection in a subject in need thereof by administering to the subject a formulation having a therapeutically effective amount of a compound of the Formula XIX represented by the structure of formula 11fb:

(11fb)

The invention also encompasses methods of treating a coronavirus infection in a subject in need thereof by administering to the subject a formulation having a therapeutically effective amount of a compound of the Formula XX:

(XX)

wherein $R_4$ is independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —CH$_2$CN, NH$_2$, hydroxyl, OC(O)CF$_3$, —OCH$_2$Ph, —NHCO—$(C_1-C_4)$alkyl, COOH, —C(O)Ph, C(O)O—$(C_1-C_4)$alkyl, C(O)H, —C(O)NH$_2$ or NO$_2$; or a pharmaceutically acceptable salt, hydrate, polymorph, or isomer.

Non limiting examples of compounds of formula XX are selected from: (2-phenyl-1H-imidazol yl)(3,4,5-trimethoxyphenyl)methanone (12aa), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (2-(p-tolyl)-1H-imidazol-4-yl)(3,4,5-trimethoxyphenyl)methanone (12da), (2-(4-chlorophenyl)-1H-imidazol-4-yl)(3,4,5-trimethoxyphenyl)methanone (12fa), (2-(4-(dimethylamino)phenyl)-1H-imidazol-4-yl)(3,4,5-trimethoxyphenyl)methanone (12ga), (2-(2-(trifluoromethyl)phenyl)-1H-imidazol-4-yl)(3,4,5-trimethoxyphenyl)methanone (12ia), (2-(4-(benzyloxy)phenyl)-1H-imidazol-4-yl)(3,4,5-trimethoxyphenyl)methanone (12ja), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (12la), (2-(4-(trifluoromethyl)phenyl)-1H-imidazol-4-yl)(3,4,5-trimethoxyphenyl)methanone (12pa).

The invention also encompasses methods of treating a coronavirus infection in a subject in need thereof by administering to the subject a formulation having a therapeutically effective amount of a compound of the Formula XX represented by the structure of formula 12da:

(12da)

The invention also encompasses methods of treating a coronavirus infection in a subject in need thereof by administering to the subject a formulation having a therapeutically effective amount of a compound of the Formula XX represented by the structure of formula 12fa:

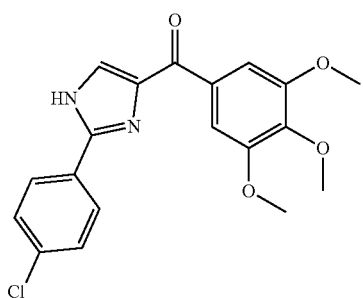

(12fa)

The invention also encompasses methods of treating a coronavirus infection in a subject in need thereof by administering to the subject a formulation having a therapeutically effective amount of a compound of the Formula XXI:

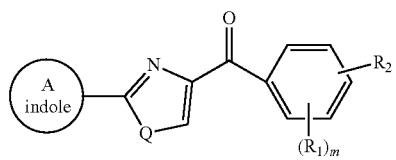

(XXI)

wherein
A is indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —CH$_2$CN, NH$_2$, hydroxyl, OC(O)CF$_3$, —OCH$_2$Ph, —NHCO—$(C_1-C_4)$alkyl, COOH, —C(O)Ph, C(O)O—$(C_1-C_4)$alkyl, C(O)H, —C(O)NH$_2$ or NO$_2$;
Q is NH;
R$_1$ and R$_2$ are independently hydrogen, $(C_1-C_4)$alkyl, halo $(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —CH$_2$CN, NH$_2$, hydroxyl, OC(O)CF$_3$, —OCH$_2$Ph, —NHCO—$(C_1-C_4)$alkyl, COOH, —C(O)Ph, C(O)O—$(C_1-C_4)$alkyl, C(O)H, —C(O)NH$_2$ or NO$_2$; and
m is 1-4; or a pharmaceutically acceptable salt, hydrate, polymorph, or isomer thereof.

In one embodiment of the method, A ring of compound of formula XXI is substituted 5-indolyl. In another embodiment the substitution is —(C=O)-Aryl. In another embodiment, the aryl is 3,4,5-(OCH$_3$)$_3$-Ph. In another embodiment, A ring of compound of formula XXI is 3-indolyl. In another embodiment, A ring of compound of formula XXI is 5-indolyl. In another embodiment, A ring of compound of formula XXI is 2-indolyl. Non limiting examples of compounds of formula XXI are selected from: (5-(4-(3,4,5-trimethoxybenzoyl)-1H-imidazol-2-yl)-1H-indol-2-yl)(3,4,5-trimethoxyphenyl)methanone (15xaa); (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); 2-(1H-indol-3-yl)-1H-imidazol-4-yl)(3,4,5-trimethoxyphenyl)methanone (17ya); (2-(1H-indol-2-yl)thiazol-4-yl)(3,4,5-trimethoxyphenyl)methanone (62a); and (2-(1H-indol-5-yl)thiazol-4-yl)(3,4,5-trimethoxyphenyl)methanone (66a).

A particularly preferred method of treating a coronavirus infection of the invention uses at least one compound of formula XXI including 2-(1H-indol-1-yl)-1H-imidazol-4-yl)(3,4,5-trimethoxyphenyl)methanone; 2-(1H-indol-2-yl)-1H-imidazol-4-yl)(3,4,5-trimethoxyphenyl)methanone; 2-(1H-indol-3-yl)-1H-imidazol-4-yl)(3,4,5-trimethoxyphenyl)methanone (17ya); 2-(1H-indol-4-yl)-1H-imidazol-4-yl)(3,4,5-trimethoxyphenyl)methanone; 2-(1H-indol-5-yl)-1H-imidazol-4-yl)(3,4,5-trimethoxyphenyl)methanone; 2-(1H-indol-6-yl)-1H-imidazol-4-yl)(3,4,5-trimethoxyphenyl)methanone; or 2-(1H-indol-7-yl)-1H-imidazol-4-yl)(3,4,5-trimethoxyphenyl)methanone.

The invention also encompasses methods of treating a coronavirus infection in a subject in need thereof by administering to the subject a formulation having a therapeutically effective amount of a compound of the Formula XXIa:

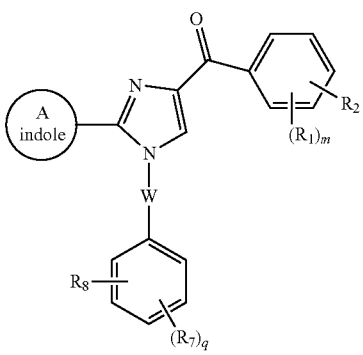

(XXIa)

wherein
W is C=O, C=S, SO$_2$, or S=O;
A is indolyl optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —CH$_2$CN, NH$_2$, hydroxyl, OC(O)CF$_3$, —OCH$_2$Ph, —NHCO—$(C_1-C_4)$alkyl, COOH, —C(O)Ph, C(O)O—$(C_1-C_4)$alkyl, C(O)H, —C(O)NH$_2$ or NO$_2$;
R$_1$ and R$_2$ are independently hydrogen, $(C_1-C_4)$alkyl, halo $(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —CH$_2$CN, NH$_2$, hydroxyl, OC(O)CF$_3$, —OCH$_2$Ph, —NHCO—$(C_1-C_4)$alkyl, COOH, —C(O)Ph, C(O)O—$(C_1-C_4)$alkyl, C(O)H, —C(O)NH$_2$ or NO$_2$;
R$_7$ and R$_8$ are independently hydrogen, $(C_1-C_4)$alkyl, halo $(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —CH$_2$CN, NH$_2$, hydroxyl, OC(O)CF$_3$, —OCH$_2$Ph, —NHCO—$(C_1-C_4)$alkyl, COOH, —C(O)Ph, C(O)O—$(C_1-C_4)$alkyl, C(O)H, —C(O)NH$_2$ or NO$_2$;
m is 1-4; and
q is 1-4; or a pharmaceutically acceptable salt, hydrate, polymorph, or isomer thereof.

Non limiting examples of compounds of formula XXIa are selected from: (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); (1-(phenylsulfonyl)-2-(1-(phenylsulfonyl)-1H-indol-3-yl)-1H-imidazol yl)(3,4,5-trimethoxyphenyl)methanone (17yaa).

The invention also encompasses methods of treating a coronavirus infection in a subject in need thereof by administering to the subject a formulation having a therapeutically effective amount of a compound of the Formula XXII:

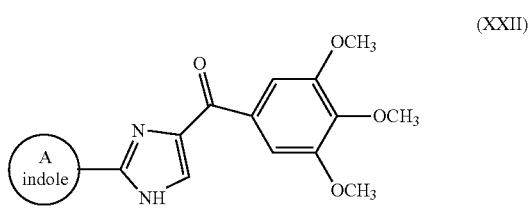

(XXII)

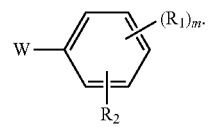

wherein

A is indolyl optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —C(O)$NH_2$ or $NO_2$;

or a pharmaceutically acceptable salt, hydrate, polymorph, or isomer thereof.

In one embodiment of the method, A ring of compound of formula XXII is substituted 5-indolyl. In another embodiment the substitution is —(C═O)-Aryl. In another embodiment, the aryl is 3,4,5-$(OCH_3)_3$-Ph. In another embodiment, A ring of compound of formula XXII is 3-indolyl. Non limiting examples of compounds of formula XXII are selected from: (5-(4-(3,4,5-trimethoxybenzoyl)-1H-imidazol-2-yl)-1H-indol-2-yl)(3,4,5-trimethoxyphenyl)methanone (15xaa); and (2-(1H-indol-3-yl)-1H-imidazol-4-yl)(3,4,5-trimethoxyphenyl)methanone (17ya).

The invention also encompasses methods of treating a coronavirus infection in a subject in need thereof by administering to the subject a formulation having a therapeutically effective amount of a compound of the Formula XXI or XXII represented by the structure of formula 17ya:

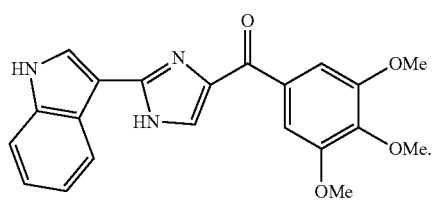

(17ya)

In one embodiment of the method, $R_4$ and $R_5$ of compounds of formula XIII-XVI are hydrogens. Non-limiting examples of compounds of formula XIII-XVI wherein $R_4$ and $R_5$ are hydrogens are selected from (2-phenyl-1H-imidazol-4-yl)(3,4,5-trimethoxyphenyl)methanone (12aa); (4-methoxyphenyl)(2-phenyl-1H-imidazol-4-yl)methanone (12ab); (3-methoxyphenyl)(2-phenyl-1H-imidazol-4-yl)methanone (12ac); (3,5-dimethoxyphenyl)(2-phenyl-1H-imidazol-4-yl)methanone (12ad); (3,4-dimethoxyphenyl)(2-phenyl-1H-imidazol-4-yl)methanone (12ae); (4-fluorophenyl)(2-phenyl-1H-imidazol-4-yl)methanone (12af); (3-fluorophenyl)(2-phenyl-1H-imidazol-4-yl)methanone (12ag); (2-phenyl-1H-imidazol-4-yl)(p-tolyl)methanone (12ah); and (2-phenyl-1H-imidazol-4-yl)(m-tolyl)methanone (12ai).

In one embodiment of the method, P of compound of formula XII is H and Q is

In another embodiment W is C═O. In another embodiment, W of compound of formula XVIII is C═O. Non-limiting examples of compound of formula XVIII wherein W is C═O are selected from (4-methoxyphenyl)(2-phenyl-1H-imidazol-1-yl)methanone (12aba) and (2-phenyl-1H-imidazol-1-yl)(3,4,5-trimethoxyphenyl)methanone (12aaa).

In one embodiment of the method, the compounds of this invention are the pure (E)-isomers. In another embodiment, the compounds of this invention are the pure (Z)-isomers. In another embodiment, the compounds of this invention are a mixture of the (E) and the (Z) isomers. In one embodiment, the compounds of this invention are the pure (R)-isomers. In another embodiment, the compounds of this invention are the pure (S)-isomers. In another embodiment, the compounds of this invention are a mixture of the (R) and the (S) isomers.

The compounds of the present invention can also be present in the form of a racemic mixture, containing substantially equivalent amounts of stereoisomers. In another embodiment, the compounds of the present invention can be prepared or otherwise isolated, using known procedures, to obtain a stereoisomer substantially free of its corresponding stereoisomer (i.e., substantially pure). As used herein, the term "substantially pure" refers to stereoisomer is at least about 95% pure in one isomer. Alternatively, the stereoisomer purity may be at least about 98% pure, and more preferably at least about 99% pure.

Compounds can also be in the form of a hydrate, which means that the compound further includes a stoichiometric or non-stoichiometric amount of water bound by non-covalent intermolecular forces.

The invention includes "pharmaceutically acceptable salts" of the compounds used in the method of the invention, which may be produced, by reaction of a compound of this invention with an acid or base. Certain compounds, particularly those possessing acid or basic groups, can also be in the form of a salt, preferably a pharmaceutically acceptable salt. As used herein, the term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically-acceptable salts of amines of compounds used in the method of the invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

Examples of organic salts of amines include, but are not limited to, aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

Examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

Examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

Typical salts include, but are not limited to, hydrofluoric, hydrochloric, hydrobromic, hydroiodic, boric, nitric, perchloric, phosphoric, sulfuric, acetate, citrate, maleate, malate, or mesylate. Preferred salts include hydrofluoric, hydrochloric, hydrobromic, hydroiodic, acetate, citrate, maleate, or mesylate. More preferred salts include hydrochloric, acetate, or maleate.

The salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of an existing salt for another ion or suitable ion-exchange resin.

The compounds used in the methods of the invention were synthesized using the methodology described in U.S. Pat. Nos. 8,592,465; 8,822,513; 9,029,408; 9,334,242; 9,447,049; and 10,301,285 and US publication No. 2020/24270, hereby incorporated by reference.

Pharmaceutical Composition

The methods of the invention include the administration of a pharmaceutical composition including a pharmaceutically acceptable carrier and at least one compound described herein. Typically, the pharmaceutical composition may include a compound or its pharmaceutically acceptable salt, and at least one pharmaceutically acceptable excipient. The term "pharmaceutically acceptable excipient" refers to any suitable adjuvants, carriers, excipients, flavorant, or stabilizers, and can be used in pharmaceutical formulations either in solid or liquid form. Such forms include, but are not limited to, tablets, capsules, powders, solutions, suspensions, or emulsions.

The amount of compound used in the method and the dosage regimen for treating a disease condition depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods.

Typically, the formulations have from about 0.01 to about 99 percent by weight of at least one compound by weight, preferably from about 20 to 75 percent of active compound (s), together with the adjuvants, carriers and/or excipients. While individual needs may vary, determination of optimal ranges of effective amounts of each component is within the skill of the art. Typical daily dosages include about 2 mg to about 200 mg or about 1 mg to about 100 mg, preferred daily dosages include about 4 mg to about 90 mg, and the most preferred dosages include about 4 mg to about 80 mg of the compound. Other preferred dosages include the antiviral compound in an amount of about 4 mg to about 45 mg, or 9 mg to about 18 mg. Alternatively, a dose is from about 0.01 to 150 mg/kg body weight, preferably from about 1 mg to about 100 mg/kg body weight, and more preferably from about 2 to 50 mg/kg body weight, may be appropriate. The daily dose can be administered in one to four doses per day. Treatment regimen for the administration of the compounds of the present invention can also be determined readily by those with ordinary skill in art. That is, the frequency of administration and size of the dose can be established by routine optimization, preferably while minimizing any side effects.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a subject's condition, a maintenance dose of a compound, composition or formulation may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The methods may include "additional therapeutic agents" including, but are not limited to, immune therapies (e.g., interferon), therapeutic vaccines, antifibrotic agents, anti-inflammatory agents such as corticosteroids or NSAIDs, bronchodilators such as beta-2 adrenergic agonists and xanthines (e.g., theophylline), mucolytic agents, anti-muscarinics, anti-leukotrienes, inhibitors of cell adhesion (e.g., ICAM antagonists), anti-oxidants (e.g., N-acetylcysteine), cytokine agonists, cytokine antagonists, lung surfactants and/or antimicrobial and anti-viral agents (e.g., ribavirin and amantidine). The methods of the invention may also be used in combination with gene replacement therapy.

The methods of the invention may be administered in conjunction with other antiviral therapies to treat the infection or disease associated with the coronavirus infection, e.g., combination therapy. Suitable antiviral agents contemplated for use in combination with the methods of the invention may include nucleoside and nucleotide reverse transcriptase inhibitors (NRTIs), non-nucleoside reverse transcriptase inhibitors (NNRTIs), protease inhibitors and other antiviral drugs. Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-c alanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Other antiviral agents include, but are not limited to, neuraminidase inhibitors, hemagglutinin inhibitor, hydroxychloroquine, azithromycin, or medications that modulate the immune system or host cell factors such dexamethasone. Examples include, but are not limited to, favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, and valaciclovir. An embodiment of the method further comprises an additional therapy such as a remdesivir and/or dexamethasone. An embodiment of the method further comprises an additional therapy such as casirivimab plus imdevimab. An embodiment of the method further comprises an additional therapy such as bamlanivimab.

The methods of treating coronavirus infections may further comprise other therapies. For example, the methods may include a second antiviral therapy such as a neuraminidase inhibitor, remdesivir, hydroxychloroquine, azithromycin, or hemagglutinin inhibitor. Other therapies included in the methods are medications that modulate the immune system or host cell factors such as dexamethasone; corticosteroids; an IL-6 inhibitor such as tocilizumab; interferons; an IL-1 inhibitor; or a kinase inhibitor such as baricitinib. The methods may further comprise an antibody therapy such as high titer COVID-19 convalescent plasma, IVIG, a monoclonal antibody therapy such as casirivimab plus imdevimab, bamlanivimab, or bamlanivimab plus etesevimab. The methods may further comprise tocilizumab or baricitinib. The methods may further comprise an additional therapy such as high title COVID-19 convalescent plasma; IVIG; casirivimab plus imdevimab; bamlanivimab; or bamlanivimab plus etesevimab. The methods may include a second antiviral therapy that is at least one of favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir. The methods may include a second therapy that is at least one of vitamins C or D, zinc, famotidine, ivermectin, or angiotensin converting enzyme inhibitor (ACEI) or angiotensin receptor binding (ARB) agent.

The solid unit dosage forms can be of the conventional type. The solid form can be a capsule and the like, such as an ordinary gelatin type containing the compounds and a carrier. Carriers include, but are not limited to, lubricants and inert fillers such as, castor oil and similar materials, lactose, sucrose, or cornstarch. The formulations may be tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

The invention can be mixed at cold temperatures, room temperature, or elevated temperatures with a liquid carrier such as a fatty oil, castor oil, or other similar oil to manufacture tablets, capsules, and the like.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, the formulation may include excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Typical compositions according to the present invention are prepared so that an oral dosage unit contains between about 1 mg and 100 mg of active compound, and preferred oral compositions contain between 1 mg and 50 mg of active compound.

The formulations may be orally administered with an inert diluent, or with an assimilable edible carrier, or they can be enclosed in hard or soft shell capsules, or they can be compressed into tablets, or they can be incorporated directly with the food of the diet. A preferred formulation is an oral formulation.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions used in the method of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

The formulation may also be administered parenterally. Solutions or suspensions of these formulations can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the formulations may be in solution or suspension may be packaged in a pressurized aerosol container together with suitable propellants, for example, hydrocarbon propellants like propane, butane, or isobutane with conventional adjuvants. The formulations also may be administered in a non-pressurized form such as in a nebulizer or atomizer.

When administering the formulations in the methods of the invention, the formulations may be administered systemically or sequentially. Administration can be accomplished in any manner effective for delivering the compounds or the pharmaceutical compositions to the site of viral infection. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

The invention is directed to methods of treating coronavirus infections and anti-viral formulations with the compounds and formulations described above. The compounds and formulations thereof have utility in treating viral infections by disrupting microtubule polymerization. The formulations may optionally comprise additional active ingredients, whose activity is useful for treating coronavirus viral infections, treat adverse effect associated with the compounds or dosages of a particular formulation, and/or delay or extend the release of the ingredients.

In particular, the methods of the invention may be used to treat infections caused by viruses including those of the superfamilies of Coronaviridae. Also, the methods of the invention may be used to treat infections caused by viruses including, but not limited to, SARS, MERS-CoV, and COVID-19. Preferably, the methods of the invention treat viral infections caused by SARS-CoV, MERS-CoV, or COVID-19. More preferably, the methods of the invention treat viral infections caused by COVID-19 (SARS-CoV-2).

The methods of the invention may be used to treat infections caused by SARS-CoV, MERS-CoV, or SARS-CoV-2, and in particular SARS-CoV-2 infection. The methods of the invention may be used to treat subjects with SARS-CoV-2 infection at high risk for acute respiratory distress syndrome (ARDS) or severe acute respiratory syndrome (SARS). The subject may have a SARS-CoV-2 infection that reduces mortality. Another embodiment of the invention encompasses methods wherein treating a subject with SARS-CoV-2 infection at high risk for acute respiratory distress syndrome (ARDS) or severe acute respiratory syndrome (SARS) reduces mortality. Another embodiment of the invention encompasses methods wherein treating a subject with SARS-CoV-2 infection reduces morbidity. Another embodiment of the invention encompasses methods wherein treating a subject with SARS-CoV-2 infection at high risk for acute respiratory distress syndrome (ARDS) or severe acute respiratory syndrome (SARS) reduces morbidity. Another embodiment of the invention encompasses methods wherein treating a subject with SARS-CoV-2 infection reduces respiratory failure, days in ICU, days on mechanical ventilator, or improves WHO Ordinal Scale for Clinical Improvements. Another embodiment of the invention encompasses methods wherein treating a subject with SARS-CoV-2 infection at high risk for acute respiratory distress syndrome (ARDS) or severe acute respiratory syndrome (SARS) reduces respiratory failure, days in ICU, days on mechanical ventilator, or improves WHO Ordinal Scale for Clinical Improvements. Another embodiment of the invention encompasses methods wherein treating a subject with SARS-CoV-2 infection reduces mortality or respiratory failure in subjects >60 years of age. Another embodiment of the invention encompasses methods wherein treating a subject with SARS-CoV-2 infection at high risk for acute respiratory distress syndrome (ARDS) or severe acute respiratory syndrome (SARS) reduces mortality or respiratory failure in subjects >60 years of age. Another embodiment of the invention encompasses methods wherein treating a subject with SARS-CoV-2 infection reduces mortality or respiratory failure when dosed in combination with remdesivir and/or dexamethasone. Another embodiment of the invention encompasses methods wherein treating a subject with SARS-CoV-2 infection at high risk for acute respiratory distress syndrome (ARDS) or severe acute respiratory syndrome (SARS) reduces mortality or respiratory failure when dosed in combination with remdesivir and/or dexamethasone.

The invention encompasses methods for treating coronavirus infections in a subject in need thereof comprising administering to the subject a formulation having a compound described herein or a pharmaceutically acceptable salt, hydrate, polymorph, or isomer thereof in a therapeutically effective amount to treat the coronavirus infection. The methods include at least one of compound 12db, compound 11cb, compound 11fb, compound 12da, compound 12fa, compound 12fb, compound 12cb, compound 55, compound 66a, or compound 17ya. In a particular method, the method includes compound 17ya.

As used herein unless otherwise stated, the term "subject or patient" refers to any mammalian patient, including without limitation, humans, other primates, dogs, cats, horses, cows, sheep, pigs, rats, mice, and other rodents. In particular, the subject is a human, and alternatively may be only male or only female.

When administering the compounds and formulations described herein, the formulations can be administered systemically or directly to a specific site where the viral infection is present. Administration may be accomplished in any manner effective for delivering the compounds or the pharmaceutical compositions to the viral infection site. Administration methods include, but are not limited to, oral, topical, transdermal, parenteral, subcutaneous, intravenous, intramuscular, intraperitoneal, intranasal, by intracavitary or intravesical instillation, intraocular, intraarterial, intralesional, or by application to the mucous membrane. Mucous membranes include those found in the nose, throat, and/or bronchial tubes, among others. Preferably, the formulation is administered orally. Administration may be simultaneous or sequential with additional antiviral compounds or formulations, or treatments used to address side effects associated with the compounds or dosages.

Treatment of COVID-19 with compound 17ya had significant biological advantages over treatment with placebo. For example, at least about 30% to about 100% of compound 17ya treated patients were kept alive without respiratory failure (primary endpoint) versus the patients treated with "placebo" (existing standard of care—remdesivir, dexamethasone, convalescent plasma, etc.). For example, compound 17ya reduced the proportion of patients who died up to 60 days after initiation of treatment from 30% (6/20) in the placebo group to 5% (1/19) after treatment with compound 17ya. The mortality reduction is about 82% reduction in the compound 17ya treated group. Therefore, treatment with compound 17ya is expected to reduce death by about 30% to about 100% of the treated group as compared to the group treated with placebo. During the study, treatment failures (defined as death or respiratory failure) were 35% in the placebo group while the treatment failures were reduced to 15.8% in group treated with compound 17ya after 15 days of treatment. The numbers reduction improved as treatment continued where treatment failures were about 30% in the placebo treated group to 10.5% in the compound 17ya treated group after 29 days on study. The results represent a 55% reduction in treatment failures after 15 days of treatment and a 65% reduction in treatment failures after 29 days on study with compound 17ya when compared to the placebo treated group. Thus, it is expected that compound 17ya will reduce treatment failures by about 30% to about 100% during treatment. Other measures of success were observed on Covid-19 treated patients.

Treatment with compound 17ya reduced the days on mechanical ventilation from an average of 5.4 days in the placebo group to 1.6 days in the group treated with compound 17ya. Those treated with placebo had about a 3.4-fold increase in days on mechanical ventilation compared to the compound 17ya treated group. Consequently, it is expected that treatment with compound 17ya will reduce the days on mechanical ventilation by about 30% to about 100% as compared to the patients treated with placebo. Another reduction was observed with patients treated with compound 17ya with regard to the days spent in ICU. The placebo treated group spent an average of 9.6 days in ICU, while those treated with compound 17ya spent about 3 days in the ICU. The placebo treated group spent an additional 3.2-fold more days in the ICU, in contrast to those patients treated with compound 17ya. Therefore, treatment with compound 17ya is expected to reduce the days spent in ICU by about 30% to about 100%.

The study sponsor (Veru) has conducted post-hoc, sub-group analyses of the data from the study. The following additional observations are made from this study: (1) In the compound 17ya treated group there was one patient who was noncompliant with oxygen supplementation. This patient noncompliant with standard of care in this study. An analysis of the primary endpoint excluding this patient (MITT population) from the analysis shows a 30% failure rate in the Placebo group (same as Table 2) compared to a 5.6% failure rate in the compound 17ya treated group at Day 29 (lower than in Table 2). This represents an 81% reduction in treatment failures. (2) It is well recognized that older patients are at higher risk for death and respiratory failure in patients with COVID-19 compared to younger patients. In an analysis of treatment failures in patients >60 years of age showed that a statistically significant (p-value of 0.0456 (chi-square)) and clinically meaningful reduction in treatment failures were observed in the compound 17ya treated (1/11 or 9%) group compared to placebo (4/8 or 50%) in this high-risk population. (3) A risk factor for an adverse clinical outcome in a patient with COVID-19 is the severity of disease at presentation. To assess this risk factor, an analysis of patients with a WHO Score of Disease Severity ≥5 at baseline was performed. The outcome of this analysis shows a clinically meaningful reduction (78%) in mortality were observed in the compound 17ya treated (1/10 or 10%) group compared to placebo (6/13 or 46%) in this high-risk population. (4) An analysis of the days in ICU in evaluable patients showed a statistically significant (p-value of 0.0469 (t-test)) and clinically meaningful reduction in days in ICU in the compound 17ya treated (3 days; N=18 subjects) group compared to placebo (9.55 days; N=20 days). (5) Additionally, the proportion of patients that were in the ICU for ≥3 days on study is statistically significantly higher (p-value of 0.0390 (chi-square)) in the placebo group (11/20 or 55%) compared to the compound 17ya treated (4/18 or 22%) group. (6) In this study, patients were permitted to receive standard of care. At the time of the study, the standard of care included treatment with remdesivir and/or dexamethasone under an Emergency Use Authorization. There were 11 patients in the study that did not receive either remdesivir or dexamethasone (6 in the compound 17ya treated group and 5 in the placebo group). An analysis of patients that received the recognized standard of care was conducted. Specifically, the days in ICU and the days on mechanical ventilation were compared between the treatment groups. In this population, in patients that received standard of care, no patient treated with compound 17ya required admission in the ICU or mechanical ventilation and there were no mortalities in this patient group. In the placebo group, 53% (8/16) required ICU admission with an average of 9.5 days in the ICU, 20% (3/15) required mechanical ventilation with an average of 3.9 days of mechanical ventilation, and 27% (4/15) died on study.

Overall, the study sponsor proposes that compound 17ya shows strong clinically meaningful outcomes in this small, proof-of-concept, Phase 2 study with statistically significant observations in reductions in death in the ITT population and in post-hoc, high-risk sub-group analyses, and days in ICU. It is important to note that all the parameters measured in the study show clinically meaningful outcomes with compound 17ya compared to placebo and there are no parameters that do not indicate benefit with compound 17ya treatment compared to placebo although some parameters do not reach statistical significance in this small study.

Safety: The overall safety conclusions are: (1) There were no treatment related serious adverse events observed on the study; and (2) there were no treatment related adverse events observed on the study. The treatment emergent adverse events that were observed in at least 2 patients in either treatment group in the study are presented in Example 1. The treatment emergent serious adverse events observed in the study are also presented in Example 1. There is no imbalance against compound 17ya in serious adverse events observed in the study. Overall, compound 17ya was well tolerated in this patient population with no clinically relevant safety observations in the compound 17ya treated group.

The use of remdesivir and dexamethasone did not have a significant effect on patient outcomes in the study. "Significant outcome" for the purposes of the clinical trial above would be reduction in treatment failures (death or respiratory failure), increase in treatment success (alive without respiratory failure), decrease in death (all-cause mortality), decrease in days in ICU, decrease in days on mechanical ventilation, or decrease in subjects requiring mechanical ventilation, or possibly further improvements in subject outcome that may become apparent with further analysis.

Given these data, it is expected that compounds of the invention would also work to treat patients with other types of coronaviruses.

The following examples are presented in order to more fully illustrate the preferred embodiments of the invention. They should in no way, however, be construed as limiting the broad scope of the invention.

EXAMPLES

The Examples set forth below are for illustrative purposes only and are not intended to limit, in any way, the scope of the present invention.

Materials and Methods:

In Vitro Tubulin Polymerization Assay. Bovine brain tubulin (0.4 mg, >97% pure) (Cytoskeleton, Denver, Colo.) was mixed with 10 µM of the test compounds and incubated in 100 µL of general tubulin buffer (80 mM PIPES, 2.0 mM $MgCl_2$, 0.5 mM EGTA, and 1 mM GTP) at pH 6.9. The absorbance of wavelength at 340 nm was monitored every 1 min for 20 min by the SYNERGY 4 Microplate Reader (Bio-Tek Instruments, Winooski, Vt.). The spectrophotometer was set at 37° C. for tubulin polymerization.

Example 1

Treatment of Subjects with COVID-19

Efficacy: Described in this example are the results of a clinical trial (COVID-19 study) that was a Phase 2, double-blind, placebo-controlled, proof-of-concept study of approximately 40 hospitalized patients with COVID-19 at high risk for acute respiratory distress syndrome (ARDS). The primary endpoint of this study was the proportion of patients alive without respiratory failure at Day 29. Key secondary endpoints include the following: proportion of patients alive without respiratory failure at Day 15 and Day 22, all-cause mortality, days in intensive care unit (ICU), and days on mechanical ventilation. A summary of the efficacy observations in the intent to treat (ITT) population from this study are listed below. The p-values presented are from a chi-square analysis for responder analysis and t-test for continuous variables. Please note that no α was set in the Phase 2 study, however for small studies such as this, the α is generally set at 0.1. Therefore, any p-value <0.1 is considered statistically significant.

This protocol employed a responder analysis. A group of 39 subjects hospitalized for COVID-19 infection at high risk for acute respiratory distress syndrome (ARDS) were divided into two groups, a placebo group of 20 subjects and a treated group (group treated with compound 17ya) of 19 patients. The treated group was given a powder filled capsule containing 18 mg of compound 17ya taken by mouth daily until hospital discharge, up to a maximum of 21 days of dosing.

These hospitalized subjects were qualified as responders if they were alive without respiratory failure on Day 15, Day 22, and Day 29. A non-responder is a subject that EITHER died before the analysis day OR had respiratory failure on the analysis day. After a subject was discharged/deceased, to establish responder/non-responder status, a phone call was made to see if the subject was alive and had no evidence of respiratory failure on Day 15, Day 22, and Day 29 and in the safety follow-up of the study. For example, if a patient died on Day 8, they were a non-responder at Day 15, Day 22, and Day 29. If a patient had respiratory failure on Day 15, but not on Day 22 or Day 29, they would be a non-responder on Day 15, but not on Day 22 or Day 29. For this analysis, "all-cause mortality" was evaluated and anyone who died was taken as a non-responder. Responders also included subjects who were discharged from the hospital or have Grade 0-4 on the WHO Ordinal Scale for Clinical improvement on Day 15, Day 22, or Day 29 (evaluation day), and non-responders were subjects who died before the evaluation day or had Grade 5-8 on the WHO Ordinal Scale for Clinical Improvement on the evaluation day.

Primary endpoint: Compound 17ya reduced the proportion of patients that are non-responders, i.e., death or respiratory failure from 35.0% in the placebo group (7/20) to 15.8% (3/19) in the compound 17ya treated group at Day 15 (p=0.1697) and from 30.0% (6/20) in the placebo group to 10.5% (2/19) in the compound 17ya treated group at Day 29 (p=0.1322). See Table 2. This represents an approximately 55% reduction in treatment failures at Day 15 and a 65% reduction in treatment failures at Day 29 in the compound 17ya treated group compared to placebo.

TABLE 2

Proportion of subjects alive and free of respiratory failure by visit (ITT population)

| | Response | 17 ya (n = 19) | Placebo (n = 20) | Odds ratio/ 95% CI/p-value |
|---|---|---|---|---|
| Day 15 | Responder | 16 (84.2%) | 13 (65.0%) | 2.56/(0.38,17.23)/ |
| | Non-responder | 3 (15.8%) | 7 (35.0%) | 0.3342 |
| Day 22 | Responder | 16 (84.2%) | 14 (70.0%) | 2.14/(0.31,14.88)/ |
| | Non-responder | 3 (15.8%) | 6 (30.0%) | 0.4433 |
| Day 29 | Responder | 17 (89.5%) | 14 (70.0%) | 2.69/(0.36,20.39)/ |
| | Non-responder | 2 (10.5%) | 6 (30.0%) | 0.3379 |

Compound 17ya reduced the proportion of patients who died up to 60 days after initiation of treatment from 30% (6/20) in the placebo group to 5% (1/19) in the compound 17ya treated group. This is an approximately 82% reduction in mortality in the compound 17ya treated group.

Compound 17ya reduced the days on mechanical ventilation from an average of 5.4 days in the placebo group to 1.6 days in the compound 17ya treated group. This represents a 3.4-fold increase in the days on mechanical ventilation in the placebo group compared to the compound 17ya treated group. See Table 3.

Compound 17ya reduced the days in ICU from an average of 9.6 days in the placebo group to 3.0 days in the compound 17ya treated group. This represents a 3.2-fold increase in the days in the ICU in the placebo group compared to the compound 17ya treated group. See Table 3.

TABLE 3

| Days on Mechanical Ventilation | | | | |
|---|---|---|---|---|
| Treatment | N | mean | SD | P-value |
| Compound 17 ya | 19 | 1.6 | 6.64 | 0.4836 |
| Placebo | 20 | 5.4 | 10.16 | |
| Days in ICU | | | | |
| Compound 17 ya | 19 | 3.0 | 7.16 | 0.0742 |
| Placebo | 20 | 9.6 | 11.54 | |

FIG. 1 illustrates the mean WHO Ordinal Scale for Clinical Improvement by Day (0=baseline). The area under the mean curve is 153 in the group treated with compound 17ya and 182 in the Placebo group, indicating greater morbidity in the placebo population and suggesting a clinical improvement associated with receiving compound 17ya.

As the study was limited in sample size based on FDA comments received during the IND review process, the study sponsor (Veru, Inc.) has conducted post-hoc, sub-group analyses of the data from the study. The following additional observations are made from this study:

In the compound 17ya treated group there was one patient who was noncompliant with oxygen supplementation. This patient was noncompliant with standard of care in this study. An analysis of the primary endpoint excluding this patient (MITT population) from the analysis shows a 30% failure rate in the Placebo group (same as Table 2) compared to a 5.6% failure rate in the compound 17ya treated group at Day 29 (lower than in Table 2). This represents an 81% reduction in treatment failures.

It is well recognized that older patients are at higher risk for death and respiratory failure in patients with COVID-19 compared to younger patients. In an analysis of treatment failures in patients >60 years of age showed that a statistically significant and clinically meaningful reduction in treatment failures were observed in the compound 17ya treated group compared to placebo in this high-risk population.

| | N | Treatment failures at Day 29 | p-value |
|---|---|---|---|
| Compound 17 ya | 11 | 1 (9%) | 0.0456 (chi-square) |
| Placebo | 8 | 4 (50%) | |

A risk factor for an adverse clinical outcome in a patient with COVID-19 is the severity of disease at presentation. To assess this risk factor, an analysis of patients with a WHO Score of Disease Severity ≥5 at baseline was performed. The outcome of this analysis shows a statistically significant and clinically meaningful reduction in treatment failures were observed in the compound 17ya treated group compared to placebo in this high-risk population. Also, clinically meaningful reduction (78%; not shown) in mortality was observed in the compound 17ya treated (1/10 or 10%) group compared to placebo (6/13 or 46%) in this high risk population.

| | N | Treatment failures at Day 29 | p-value |
|---|---|---|---|
| Compound 17 ya | 9* | 1 (11%) | 0.0827 (chi-square) |
| Placebo | 13 | 6 (46%) | |

*one patient in the compound 17 ya treated group was noncompliant with oxygen therapy and is excluded from this modified intent to treat (MITT) analysis.

An analysis of the days in ICU in evaluable patients showed a statistically significant and clinically meaningful reduction in days in ICU in the compound 17ya treated group compared to placebo.

| | N | Mean days in ICU (± st.dev) | p-value |
|---|---|---|---|
| Compound 17 ya | 18 | 3.00 ± 7.37 | 0.0469 (t-test) |
| Placebo | 20 | 9.55 ± 12.56 | |

Additionally, the proportion of patients that were in the ICU for ≥3 days on study is statistically significantly higher in the placebo group compared to the compound 17ya treated group.

| | N | Treatment failures at Day 29 | p-value |
|---|---|---|---|
| Compound 17 ya | 18 | 4 (22%) | 0.0390 (chi-square) |
| Placebo | 20 | 11 (55%) | |

In this study, patients were permitted to receive standard of care. At the time of the study, the standard of care included treatment with remdesivir and/or dexamethasone under an Emergency Use Authorization. There were eleven patients in the study that did not receive either remdesivir or dexamethasone (6 in the compound 17ya treated group and 5 in the placebo group). An analysis of patients that received the recognized standard of care was conducted. Specifically, the days in ICU and the days on mechanical ventilation were compared between the treatment groups. In this population, in patients that received standard of care, no patient treated with compound 17ya required admission in the ICU or mechanical ventilation and there were no mortalities in this patient group. In the placebo group, 53% (8/16) required ICU admission with an average of 9.5 days in the ICU, 20% (3/15) required mechanical ventilation with an average of 3.9 days of mechanical ventilation, and 27% (4/15) died on study.

Overall, the study sponsor proposes that compound 17ya shows strong clinically meaningful outcomes in this small, proof-of-concept, Phase 2 study with statistically significant observations in reductions in death in the ITT population and in post-hoc, high-risk sub-group analyses, and days in ICU. It is important to note that all the parameters measured in the study show clinically meaningful outcomes with compound 17ya compared to placebo and there are no parameters that do not indicate benefit with compound 17ya treatment compared to placebo although some parameters do not reach statistical significance in this small study.

Safety: The overall safety conclusions are: (1) There were no treatment related serious adverse events observed on the study; (2) There were no treatment related adverse events observed on the study; and (3) The treatment emergent adverse events that were observed in at least 2 patients in either treatment group in the study are presented in Table 4. There is no imbalance against compound 17ya in adverse events observed in the study.

TABLE 4

COVID-19 Study: Treatment Emergent Adverse Events Observed in ≥2 Patients in Either Treatment Group by Preferred Term

| Preferred Term | Compound 17 ya 18 mg (n = 19) N (%)/events | Placebo (n = 20) N (%)/events |
|---|---|---|
| Any | 10 (52.6)/27 | 11 (55.0)/41 |
| Constipation | 2 (10.5)/2 | 2 (10.0)/2 |
| Septic shock | 1 (5.3)/1 | 2 (10.0)/2 |
| Alanine aminotransferase increased | 1 (5.3)/1 | 2 (10.0)/2 |
| Aspartate aminotransferase increased | 2 (10.5)/2 | 1 (5.0)/1 |
| Acute kidney injury | 0 | 2 (10.0)/2 |
| Pneumomediastinum | 0 | 2 (10.0)/2 |
| Pneumothorax | 1 (5.3)/1 | 3 (15.0)/3 |
| Respiratory failure | 0 | 4 (20.0)/4 |

The treatment emergent serious adverse events observed in the study are presented in Table 5. There is no imbalance against compound 17ya in serious adverse events observed in the study.

TABLE 5

COVID-19 Study: Serious Adverse Events Observed by System Organ Class and Preferred

| System Organ Class Preferred Term | Compound 17 ya 18 mg (n = 19) N (%)/events | Placebo (n = 20) N (%)/events |
|---|---|---|
| Any | 3 (15.8)/3 | 4 (20.0)/4 |
| Cardiac disorders | 1 (5.3)/1 | 0 |
| Cardiac arrest | 1 (5.3)/1 | 0 |
| Infections and infestations | 1 (5.3)/1 | 2 (10.0)/2 |
| COVID-19 | 0 | 1 (5.0)/1 |
| Septic shock | 1 (5.3)/1 | 1 (5.0)/1 |
| Nervous system disorders | 0 | 1 (5.0)/1 |
| Encephalopathy | 0 | 1 (5.0)/1 |
| Renal and urinary disorders | 0 | 1 (5.0)/1 |
| Acute kidney injury | 0 | 1 (5.0)/1 |
| Respiratory, thoracic and mediastinal disorders | 1 (5.3)/1 | 2 (10.0)/2 |
| Epistaxis | 1 (5.3)/1 | 0 |
| Respiratory failure | 0 | 2 (10.0)/2 |

Overall, compound 17ya was well tolerated in this patient population with no clinically relevant safety observations in the compound 17ya treated group.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating a coronavirus infection in a subject in need thereof by administering to the subject a formulation having a therapeutically effective amount of a compound of Formula (I):

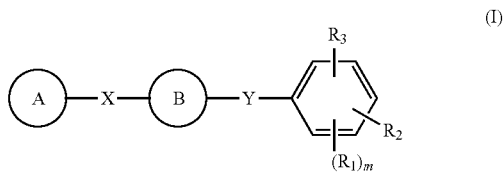

wherein
A is phenyl, indolyl, or indazolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —C(O)$NH_2$ or $NO_2$;
B is an imidazole or benzimidazole, optionally substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;
$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —C(O)$NH_2$ or $NO_2$;
X is a bond or NH;
Y is —C═O; and
m is 1-3, or a pharmaceutically acceptable salt, or isomer thereof.

2. The method according to claim 1, wherein A is phenyl or indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —C(O)$NH_2$ or $NO_2$;
B is an imidazole, optionally substituted with at least one of $(C_1-C_4)$alkyl;
$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —C(O)$NH_2$ or $NO_2$;
X is a bond or NH;
Y is —C═O; and
m is 1-3, or a pharmaceutically acceptable salt, or isomer thereof.

3. The method according to claim 1, wherein A is phenyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —C(O)$NH_2$ or $NO_2$;
B is an imidazole, optionally substituted with at least one of $(C_1-C_4)$alkyl;

$R_1$, $R_2$ and $R_3$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —CH$_2$CN, NH$_2$, hydroxyl, OC(O)CF$_3$, —OCH$_2$Ph, —NHCO—$(C_1\text{-}C_4)$alkyl, COOH, —C(O)Ph, C(O)O—$(C_1\text{-}C_4)$alkyl, C(O)H, —C(O)NH$_2$ or NO$_2$;

X is a bond or NH;

Y is —C=O; and m is 1-3, or a pharmaceutically acceptable salt, or isomer thereof.

4. The method according to claim 1, wherein A is indolyl, optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —CH$_2$CN, NH$_2$, hydroxyl, OC(O)CF$_3$, —OCH$_2$Ph, —NHCO-alkyl, COOH, —C(O)Ph, C(O)O—$(C_1\text{-}C_4)$alkyl, C(O)H, —C(O)NH$_2$ or NO$_2$;

B is an imidazole, optionally substituted with at least one of $(C_1\text{-}C_4)$alkyl;

$R_1$, $R_2$ and $R_3$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —CH$_2$CN, NH$_2$, hydroxyl, OC(O)CF$_3$, —OCH$_2$Ph, —NHCO—$(C_1\text{-}C_4)$alkyl, COOH, —C(O)Ph, C(O)O—$(C_1\text{-}C_4)$alkyl, C(O)H, —C(O)NH$_2$ or NO$_2$;

X is a bond or NH;

Y is —C=O; and m is 1-3, or a pharmaceutically acceptable salt, or isomer thereof.

5. The method according to claim 1, wherein A is indolyl, optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —CH$_2$CN, NH$_2$, hydroxyl, OC(O)CF$_3$, —OCH$_2$Ph, —NHCO—$(C_1\text{-}C_4)$alkyl, COOH, —C(O)Ph, C(O)O—$(C_1\text{-}C_4)$alkyl, C(O)H, —C(O)NH$_2$ or NO$_2$;

B is an imidazole, optionally substituted with at least one of $(C_1\text{-}C_4)$alkyl;

$R_1$, $R_2$ and $R_3$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —CH$_2$CN, NH$_2$, hydroxyl, OC(O)CF$_3$, —OCH$_2$Ph, —NHCO—$(C_1\text{-}C_4)$alkyl, COOH, —C(O)Ph, C(O)O—$(C_1\text{-}C_4)$alkyl, C(O)H, —C(O)NH$_2$ or NO$_2$;

X is a bond;

Y is —C=O; and m is 1-3, or a pharmaceutically acceptable salt, or isomer thereof.

6. A method of treating a coronavirus infection in a subject in need thereof by administering to the subject a formulation having a therapeutically effective amount of a compound of the Formula VII:

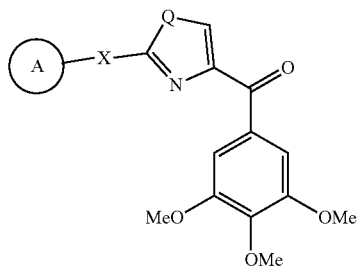

(VII)

wherein

X is a bond or NH;

Q is NH and

A is a phenyl, indolyl, or indazolyl ring optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —CH$_2$CN, NH$_2$, hydroxyl, OC(O)CF$_3$, —OCH$_2$Ph, —NHCO—$(C_1\text{-}C_4)$alkyl, COOH, —C(O)Ph, C(O)O—$(C_1\text{-}C_4)$alkyl, C(O)H, —C(O)NH$_2$ or NO$_2$; or a pharmaceutically acceptable salt, or isomer thereof.

7. The method according to claim 6, wherein X is a bond.

8. The method according to claim 6, wherein X is NH.

9. The method according to claim 6, wherein X is a bond; Q is NH; and A is an indolyl ring optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —CH$_2$CN, NH$_2$, hydroxyl, OC(O)CF$_3$, —OCH$_2$Ph, —NHCO—$(C_1\text{-}C_4)$alkyl, COOH, —C(O)Ph, C(O)O—$(C_1\text{-}C_4)$alkyl, C(O)H, —C(O)NH$_2$ or NO$_2$; or a pharmaceutically acceptable salt, or isomer thereof.

10. A method of treating a coronavirus infection in a subject in need thereof by administering to the subject a formulation having a therapeutically effective amount of a compound of the Formula VII(c):

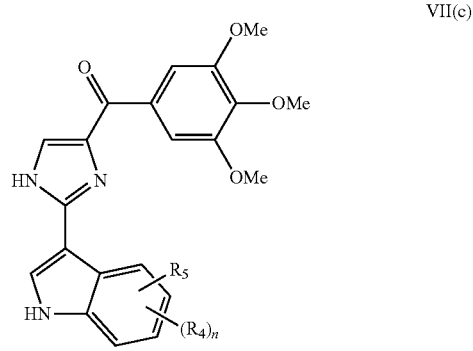

VII(c)

wherein $R_4$ and $R_5$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —CH$_2$CN, NH$_2$, hydroxyl, OC(O)CF$_3$, —OCH$_2$Ph, —NHCO—$(C_1\text{-}C_4)$alkyl, COOH, —C(O)Ph, C(O)O—$(C_1\text{-}C_4)$alkyl, C(O)H, —C(O)NH$_2$ or NO$_2$; and n is 1-4; or a pharmaceutically acceptable salt, or isomer thereof.

11. A method of treating a coronavirus infection in a subject in need thereof by administering to the subject a formulation having a therapeutically effective amount of a compound 17ya represented:

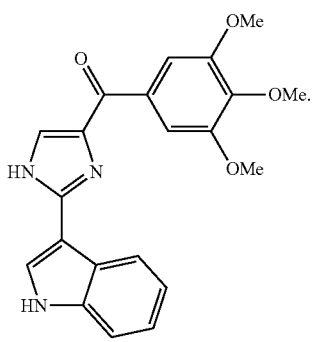

(17ya)

12. The method according to claim 1, wherein the coronavirus infection is caused by SARS-CoV, MERS-CoV, or SARS-CoV-2.

13. The method according to claim 1, wherein the coronavirus infection is caused by SARS-CoV-2.

14. The method according to claim 13, wherein the subject with SARS-CoV-2 infection is at high risk for acute respiratory distress syndrome (ARDS) or severe acute respiratory syndrome (SARS).

15. The method according to claim 13, wherein the method reduces mortality as compared to a patient population treated with placebo.

16. The method according to claim 13, wherein the method reduces morbidity as compared to a patient population treated with placebo.

17. The method according to claim 16, wherein the method reduces respiratory failure, days in ICU, days on mechanical ventilator, or improves WHO Ordinal Scale for Clinical Improvements as compared to a patient population treated with placebo.

18. The method according to claim 13, wherein the method reduces mortality or respiratory failure in subjects >60 years of age as compared to a patient population treated with placebo.

19. The method according to claim 13, wherein the method reduces mortality or respiratory failure when dosed in combination with remdesivir and/or dexamethasone as compared to a patient population treated with placebo.

20. The method according to claim 13, further comprising a second therapy.

21. The method according to claim 20, wherein the second therapy is remdesivir, dexamethasone or another corticosteroid, or remdesivir plus a corticosteroid.

22. The method according to claim 20, wherein the second therapy is a medication that modulates the immune system or host cell factors, such as dexamethasone or another corticosteroid, an IL-6 inhibitor such as tocilizumab, interferons, an IL-1 inhibitor, or a kinase inhibitor such as baricitinib.

23. The method according to claim 20, wherein the second therapy is an antibody therapy such as high titer COVID-19 convalescent plasma, IVIG, a monoclonal antibody therapy such as casirivimab plus imdevimab, bamlanivimab, or bamlanivimab plus etesevimab.

24. The method according to claim 20, wherein the second therapy is a second antiviral therapy that is at least one of favipiravir, lopinavir, ritonavir, remdesivir, janus kinase inhibitors, hydroxychloroquine, azithromycin, a neuraminidase inhibitor, amantadine, rimantadine, a hemagglutinin inhibitor, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir.

25. The method according to claim 20, wherein the second therapy is at least one of vitamins C or D, zinc, famotidine, ivermectin, or angiotensin converting enzyme inhibitor (ACEI) or angiotensin receptor binding (ARB) agent.

26. The method according to claim 13, wherein the compound is administered in an amount of about 1 to about 100 mg.

27. The method according to claim 13, wherein the compound is administered in an amount of about 4 mg to about 90 mg.

28. The method according to claim 13, wherein the compound is administered in an amount of about 4 mg to about 45 mg.

29. The method according to claim 1 further comprising a pharmaceutically acceptable excipient.

30. The method according to claim 1, wherein the subject has a WHO score of 5 or more.

31. The method according to claim 1, wherein the subject is receiving standard care.

32. The method according to claim 1, wherein the subject is receiving standard care prior to administration of the compound of formula (I).

33. The method according to claim 1, wherein the subjects are male.

* * * * *